US012709726B2

(12) United States Patent
Katti et al.

(10) Patent No.: US 12,709,726 B2
(45) Date of Patent: Aug. 18, 2026

(54) HORIZONTAL FLUID FLOW BIOREACTOR FOR CANCER RESEARCH

(71) Applicant: NDSU RESEARCH FOUNDATION, Fargo, ND (US)

(72) Inventors: Dinesh Ramanath Katti, Fargo, ND (US); Kalpana S. Katti, Fargo, ND (US); Haneesh Jasuja, Fargo, ND (US)

(73) Assignee: NDSU RESEARCH FOUNDATION, Fargo, ND (US)

(*) Notice: Subject to any disclaimer, the term of this patent is extended or adjusted under 35 U.S.C. 154(b) by 680 days.

(21) Appl. No.: 18/300,178

(22) Filed: Apr. 13, 2023

(65) Prior Publication Data

US 2023/0357694 A1 Nov. 9, 2023

Related U.S. Application Data

(60) Provisional application No. 63/362,934, filed on Apr. 13, 2022.

(51) Int. Cl.

| | |
|---|---|
| ***C12M 1/00*** | (2006.01) |
| ***C12M 1/12*** | (2006.01) |
| ***C12M 3/00*** | (2006.01) |

(52) U.S. Cl.

CPC ............ *C12M 29/12* (2013.01); *C12M 23/46* (2013.01); *C12M 25/14* (2013.01); *C12M 29/20* (2013.01)

(58) Field of Classification Search

CPC ...... C12M 29/12; C12M 29/20; C12M 29/04; C12M 29/10; C12M 23/46; C12M 25/14

See application file for complete search history.

(56) References Cited

U.S. PATENT DOCUMENTS 5,459,069 A * 10/1995 Palsson ................ C07K 14/535 435/293.1

6,001,585 A * 12/1999 Gramer .................. C12M 23/24 435/243

(Continued)

OTHER PUBLICATIONS

Hasinah K Albeladi, Abeer N Al-Romanizan, Mahmoud A Hussein "Role of cross-linking processon the performance of PMMA" International Journal of Biosensors & Bioelectronics 3(3): 279-284 (Year: 2017).*

(Continued)

*Primary Examiner* — Michael L Hobbs

(74) *Attorney, Agent, or Firm* — McKee, Voorhees & Sease, PLC

(57) ABSTRACT

A horizontal flow bioreactor facilitates continuous flow conditions to cells grown on a tissue engineered scaffold. More particularly, interstitial fluid flow conditions are mimicked around cells inside the body, thereby improving the mass transfer rates of cells and providing physical stimulus to the cells. Unlike the available perfusion based vertical bioreactors where flow is vertical through scaffolds, the horizontal flow reactor enables studies on attachment of cells to substrates, tissues, and bone mimetic scaffolds. The horizontal bioreactor further aides study of cell proliferation, cell migration, cell clustering, biology of cell growth, cell response, cell filtration techniques for capturing tumor cells, the testing of drugs, and drug delivery under flow conditions. The horizontal bioreactor can mimic in vivo conditions, epithelial to mesenchymal transition (EMT), and mesenchymal to epithelial transition (MET).

9 Claims, 23 Drawing Sheets

Specification includes a Sequence Listing.

(56) References Cited

U.S. PATENT DOCUMENTS

| | | | | |
|---|---|---|---|---|
| 2010/0273258 A1* | 10/2010 | Lannutti | C12M 35/04 | 435/366 |
| 2023/0098953 A1* | 3/2023 | Peyser | C12M 29/04 | 435/297.1 |
| 2023/0295551 A1* | 9/2023 | Truong | C12M 29/10 | 435/289.1 |

OTHER PUBLICATIONS

Ambre et al., "Biomineralized hydroxyapatite nanoclay composite scaffolds with polycaprolactone for stem cell-based bone tissue engineering," J. Biomed Mater. Res. Part A: 103A, 2015, pp. 2077-2101.
Ambre et al., "In situ mineralized hydroxyapatite on amino acid modified nanoclays as novel bone biomaterials," Materials Science and Engineering C, 2011, vol. 31, pp. 1017-1029.
Ambre et al., "Nanoclay Based Composite Scaffolds for Bone Tissue Engineering Applications," Journal of Nanotechnology in Engineering and Medicine, Aug. 2010, vol. 1, No. 031013, pp. 1-9.
Ambre et al., "Nanoclays mediate stem cell differentiation and mineralized ECM formation on biopolymer scaffolds," J. Biomed. Mater. Res. Part A, 2013, pp. 1-17.
Bixel et al., "Flow Dynamics and HSPC Homing in Bone Marrow Microvessels," Cell Reports, Feb. 14, 2017, vol. 18, pp. 1804-1816.
Chang et al., "Tumor cell cycle arrest induced by shear stress: Roles of integrins and Smad," PNAS, Mar. 11, 2008, vol. 105, No. 10, pp. 3927-3932.
Chen et al., "Mechanotransduction in Response to Shear Stress," The Journal of Biological Chemistry, Jun. 25, 1999, vol. 274, No. 26. pp. 18393-18400.
Chen et al., "Suppression of transforming growth factor-β-induced apoptosis through phosphatidylinositol 3-kinase/Akt-dependent pathway," Oncogene, 1998, vol. 17, pp. 1959-1968.
Chinni et al., "CXCLI2/CXCR4 Signaling Activates Akt-I and MMP-9 Expression in Prostate Cancer Cells: The Role of Bone Microenvironment-Associated CXCLI2," The Prostate, 2006, vol. 66, pp. 32-48.
Conley-Lacomb et al., "Pharmacological targeting of CXCL12/CXCR4 signaling in prostate cancer bone metastasis," Molecular Cancer, 2016, vol. 15, No. 68, pp. 1-13.
Fischbach et al., "Engineering tumors with 3D scaffolds," Nature Methods, Oct. 2007, vol. 4, No. 10, pp. 855-860.
Hajal et al., "The effects of luminal and trans-endothelial fluid flows on the extravasation and tissue invasion of tumor cells in a 3D in vitro microvascular platform," Biomaterials, Jan. 2021, vol. 265, pp. 1-25.
Hendrix et al., "A Simple Quantitative Assay for Studying the Invasive Potential of High and Low Human Metastatic Variants," Cancer Letters, 1987, vol. 38, pp. 137-147.
Jasuja et al., "Perfusion bioreactor enabled fluid-derived shear stress conditions for novel bone metastatic prostate cancer testbed," Biofabrication, 2021, vol. 13, 15 pages.
Kar et al., "Tissue-engineered nanoclay-based 3D in vitro breast cancer model for studying breast cancer metastasis to bone," Journal of Tissue Engineering and Regenerative Medicine, 2019, vol. 13, pp. 119-130.
Kar et al., "Wnt/β-Catenin Signaling Pathway Regulates Osteogenesis for Breast Cancer Bone Metastasis: Experiments in an In Vitro Nanoclay Scaffold Cancer Testbed," ACS Biomaterials Science & Engineering, 2020, vol. 6, pp. 2600-2611.
Katti et al., "Nanostructured Biomaterials for In Vitro Models of Bone Metastasis Cancer," Current Opinion in Biomedical Engineering, Mar. 2021, vol. 17, No. 100254, pp. 1-16.
Katti et al., "Use of unnatural amino acids for design of novel organomodified clays as components of nanocomposite biomaterials," Philosophical Transactions of The Royal Society A, 2010, vol. 368, pp. 1963-1980.
Katti et al., "Vesicular delivery of crystalline calcium minerals to ECM in biomineralized nanoclay composites," Materials Research Express, 2015, vol. 2, No. 045401, pp. 1-13.
Lebrun, J., "The Dual Role of TGFβ in Human Cancer: From Tumor Suppression to Cancer Metastasis," ISRN Molecular Biology, 2012, vol. 2012, Article ID: 381428, 28 pages.
Marturano-Kruik et al., "Human bone perivascular niche-on-a-chip for studying metastatic colonization," PNAS Early Edition, 2018, vol. 115, No. 6, pp. 1-6.
Molla et al., "In vitro design of mesenchymal to epithelial transition of prostate cancer using metastasis using 3D nanoclay bone-mimetic scaffolds," Journal of Tissue Engineering and Regenerative Medicine, 2018, vol. 12, No. 3, 32 pages.
Molla et al., "Prostate Cancer Phenotype Influences Bone Mineralization at Metastasis: A Study Using an In Vitro Prostate Cancer Metastasis Testbed," JMBR plus, 2020, vol. 4, No. 2, pp. 1-14.
Motyl et al., "Expression of bcl-2 and bax in TGF-β1-induced apoptosis of L1210 leukemic cells," The European Journal of Cell Biology, Apr. 1998, vol. 75, pp. 367-374.
Munson et al., "Intersitial Flow in a 3D Microenvironment Increases Glioma Invasion by a CXCR4-Dependent Mechanism," Cancer Research, Mar. 1, 2013, vol. 73, No. 5, pp. 1536-1546.
Ohgushi et al., "Transforming Growth Factor β-Dependent Sequential Activation of Smad, Bim, and Caspase-9 Mediates Physiological Apoptosis in Gastric Epithelial Cells," Molecular and Cellular Biology, Nov. 2005, vol. 25, No. 22, pp. 10017-10028.
Ramesh et al., "Transforming growth factor β (TGFβ)-induced apoptosis," Cell Cycle, Jan. 1, 2009, vol. 8, No. 1, pp. 11-17.
Shah et al., "Intersitital Fluid Flow Increases Hepatocellular Carcinoma Cell Invasion through CXCR4/CXCL12 and MEK-ERK Signaling," PLoS ONE, Nov. 11, 2015, vol. 10, No. 11, pp. 1-17.
Shin et al., "Microfluidic assay for simultaneous culture of multiple cell types on surfaces or within hydrogels," Nature Protocols, 2012, vol. 7, No. 7, pp. 1247-1259.
Siegel et al., "Cancer Statistics, 2021," CA Cancer J Clin, 2021, vol. 71, pp. 7-33.
Sobachkin et al., "Numerical Basis of CAD-Embedded CFD," NAFEMS World Congress 2013, Feb. 2014, pp. 1-19.
Song et al., "Novel roles of Akt and mTOR in suppressing TGF-β/ALK5-mediated Smad3 activation," The EMBO Journal, 2006, vol. 25, pp. 58-69.
Sun et al., "CXCL12/CXCR4/CXCR7 chemokine axis and cancer progression," Cancer Metastasis Reviews, 2010, vol. 29., No. 4, pp. 709-722.
Sun et al., "Expression of CXCR4 and CXCL12 (SDF-1) in Human Prostate Cancers (PCa) in Vivo," Journal of Cellular Biochemistry, 2003, vol. 89, pp. 462-473.
Urbich et al., "Laminar Shear Stress Upregulates Integrin Expression Role in Endothelial Cell Adhesion and Apoptosis," Circulation Research, Oct. 13, 2000, vol. 87, pp. 683-689.
Wakefield et al., "TGF-β signaling: positive and negative effects on tumorigenesis," Current Opinion in Genetics & Development, 2002, vol. 12, pp. 22-29.
Zhang et al., "A microfluidic-based device for study of transendothelial invasion of tumor aggregates in realtime," Lab on a Chip, 2012, vol. 12, No. 16, pp. 1-6.
Zhao et al., "Roles for GP IIb/IIIa and αvβ3 integrins in MDA-MB-231 cell invasion and shear flow-induced cancer cell mechanotransduction," Cancer Letters, 2014, vol. 344, pp. 62-73.
Zheng et al., "Prostatic Carcinoma Cell Migration via Avβ3 Integrin Is Modulated by a Focal Adhesion Kinase Pathway," Cancer Research, Apr. 1, 1999, vol. 59, pp. 1655-1664.
Zheng et al., "Substrate Specificity of αvβ3 Integrin-mediated Cell Migration and Phosphatidylinositol 3-Kinase/AKT Pathway Activiation," The Journal of Biological Chemistry, Aug. 11, 2000, vol. 275, No. 32, pp. 24565-22574.

* cited by examiner

HORIZONTAL FLUID FLOW BIOREACTOR FOR CANCER RESEARCH

CROSS-REFERENCE TO RELATED APPLICATIONS

This application claims priority under 35 U.S.C. § 119 to provisional application Ser. No. 63/362,934, filed Apr. 13, 2022, herein incorporated by reference in its entirety.

STATEMENT REGARDING FEDERALLY SPONSORED RESEARCH OR DEVELOPMENT

This invention was made with government support under Grant No. 1946202-EPSCoR RII Track-1:NDACES; New Discoveries in the Advanced Interface of Computation, Science, and Engineering; Granted 7/1/2020 by National Science Foundation Grant No. 1946202-EPSCoR RII Track-1:NDACES; New Discoveries in the Advanced Interface of Computation, Science, and Engineering; Granted 7/1/2020 by National Science Foundation Grant No. U54GM128729—Design of Humanoid Testbeds of breast cancer bone metastasis; Granted 9/1/2020 by National Institutes of Health. The government has certain rights in the invention.

SEQUENCE LISTING XML

The instant application contains a sequence listing, which has been submitted in XML file format by electronic submission and is hereby incorporated by reference in its entirety. The XML file, created on Apr. 11, 2023, is named P13850US01.xml and is 16,676 bytes in size.

TECHNICAL FIELD

The present invention relates generally to a bioreactor having applications in at least the research, pharmaceutical, biotechnology companies, medicinal, and therapeutic industries. More particularly, but not exclusively, the present invention relates to a horizontal fluid flow bioreactor that aides in at least: the development of new cancer biomarkers, discovery of new drugs, personalization of medicine for cancer patients, and the researching of cancer and therapeutics.

BACKGROUND

The background description provided herein gives context for the present disclosure. Work of the presently named inventors, as well as aspects of the description that may not otherwise qualify as prior art at the time of filing, are neither expressly nor impliedly admitted as prior art.

Cancer metastasis is an ill understood concept due to lack of human samples and lack of animal models. Prostate and breast cancers are the most common bone metastasized cancers affecting mostly men and women, respectively. It is estimated that 248,530 cases of prostate cancer and 281,550 cases of invasive breast cancer diagnosed at the end of 2021 in the United States. With the advancement in therapy for primary staged cancers, the overall 5-year survival rate has now improved. However, in the case of metastasis, where cancer cells migrate to distant organs, the overall survival rate is still poor. This is considered the major cause of morbidity in patients with metastasized prostate and breast cancer cells.

Both prostate and breast cancer cells have the propensity to metastasize to the liver, brain, lungs, and bone. Bone metastasis occurs in about 80% of patients with advanced-stage prostate and breast cancers. To colonize the bone site, tumor cells invade the extracellular matrix (ECM) of the growing tumor at their primary site, intravasate into the blood circulation, and then extravasate from the blood vasculature to the bone ECM. Once established to the bone, these cancer cells majorly affect the bone remodeling process and lead to severe skeletal-related defects such as bone fracture, spinal cord compression, hypercalcemia, and pain. Lesions caused by these cancer cells after bone metastasis can be categorized into osteoblastic (excess bone formation) and osteoclastic (excess bone resorption).

Unfortunately, due to the limited understanding of cancer cell growth and migration, the treatment of advanced-stage cancer has been mainly ineffective. Such a limited understanding stems in part from a scarcity of knowledge regarding the mechanisms associated with the effects of biomechanical cues by the interstitial fluid flow on prostate cancer cell growth and migration. As a result, drug treatment options are scarce, resulting in low survival rates among individuals. The drug therapies available currently are utilized to reduce pain and improve bone stability. The drug therapeutics include bisphosphonates, which have adverse effects such as bone, joint, or muscle pain; nausea; vomiting; and diarrhea.

In vitro models have been proved beneficial for studying cancer cell progression and developing novel anticancer drugs. Currently, monoculture/2D culture is widely used to grow cell populations and cell-based assays however, 2D culture fails to recapitulate the dynamic interactions between cancer cells and bone microenvironment, due to lack of realistic complexity. Hence, 3D in vitro models have gained considerable attention, owing to their crosstalk between cells and the surrounding milieu.

3D in vitro disease models mimic more closely the pathophysiological microenvironment due to close interaction between different cell types and release of factors responsible for the generation of ECM in a precise system. 3D in vitro models bridge the gap between 2D monoculture models that do not possess in vivo structural complexity and expensive in vivo models, often failing to recapitulate the late stage of cancers.

3D in vitro disease models of prostate and breast cancer bone metastasis have been developed using polymer-nanoclay based scaffolds. These nanoclay scaffolds were incorporated into tissue-engineered constructs for the enhancement of their mechanical properties, such as: a high porosity of 86.1% with pore sizes ranging between 10-30 μm to 100-300 μm and a compressive modulus of 2.495 MPa, which is required for hard tissue growth.

Additionally, the role of interstitial fluid in prostate cancer progression to the bone using an in vitro model, a perfusion bioreactor, has been previously investigated. Known perfusion type bioreactors vertically force fluid through porous materials.

Understanding the metastatic cascade of cancer cells can prove essential to pave the way to discover novel drugs for metastatic cancers. In particular, the extravasation stage can be a critical process for cancer cells invasion to the secondary site and subsequent development of metastatic tumors. Extravasation comprises various stages, including slowly rolling, adherence to the sinusoidal capillaries, and transmigration across the capillary's endothelium.

Recently, several groups have developed microfluidic platforms to recapitulate the extravasation microenvironment that majorly focuses on the effects of biomechanical cues on tumor cell motility. In addition, Boyden chamber-Transwell assays deliver a relatively simple and high throughput system for quantifying percentage cell migration, yet do not fully recapitulate extravasation and migration behavior under physiological fluid flow conditions. While these models have provided useful insight into the migration behavior of cancer cells at their distant site, they did not adequately address the effect of interstitial fluid flow on cancer cells' migration rate and their molecular mechanisms.

Thus, there exists a need in the art for an apparatus which fluid flow closely mimics the blood flow around tissues and organs. There also exists a need in the art for an apparatus which can accurately recapitulate the effect of interstitial fluid flow on the migration of late-stage cancer cells.

SUMMARY

Increasing evidence suggests the synergistic role of biochemical and biophysical cues in cancer progression at metastases. 3D in vitro dynamic models of prostate cancer bone metastasis using a horizontal flow bioreactor to delineate the role of flow-induced shear stress on prostate cancer progression and migration, respectively at metastases, are described herein.

This horizontal flow bioreactor can mimic microenvironments for a variety of in vivo conditions, e.g., the primary site of cancer and the metastasized site of cancer. The flow conditions enabled by this bioreactor can enable migration of cancer cells from the primary tumor site to a secondary site through fluid flow mimicking the conditions of cancer metastasis. This bioreactor uniquely enables the creation of metastasis or translocation of human cells from one location to another as in the process of metastasis.

The percent cell migration rate of prostate cancer cells using the horizontal flow bioreactor increases in the presence of bone under dynamic conditions.

The following objects, features, advantages, aspects, and/or embodiments, are not exhaustive and do not limit the overall disclosure. No single embodiment need provide each and every object, feature, or advantage. Any of the objects, features, advantages, aspects, and/or embodiments disclosed herein can be integrated with one another, either in full or in part.

It is a primary object, feature, and/or advantage of the present invention to improve on or overcome the deficiencies in the art.

It is a further object, feature, and/or advantage of the present invention to mimic continuous flow conditions to cells grown on a tissue-engineered scaffold.

It is still yet a further object, feature, and/or advantage of the present invention to mimic the interstitial fluid flow conditions around cells inside the body. Interstitial fluid flow acts as a driving force for cancer cell migration in the vicinity of cancer cells proximate to the capillary pores. The mimicking of interstitial fluid flow allows for the investigation of the underlying mechanism and the role of interstitial fluid flow in cancer cell migration.

It is a further object, feature, and/or advantage of the present invention to simulate circulating tumor cells.

Depending on the type of cancer cell, interstitial flow-induced shear stress can be a critical factor in regulating the migration of said cell at its extravasation stage. For example, fluid flow rate corresponding to the physiological velocity of the interstitial fluid is optimum for better cells growth compared to high flow rate, where it can be observed suppression in the growth rate of PC3 cells due to induction in apoptosis. It is worth noting scaffold pore size and/or interconnectivity, rather than flow rate alone, can also influence the rate of shear stress.

It is still yet a further object, feature, and/or advantage to demonstrate the migration of cancer cells through transwell inserts under both dynamic and static culture conditions. The use of transwell inserts helps reveal the crucial role of interstitial fluid flow in cancer cell motility at a distant organ in ways that known microfluidic chip models cannot.

It is still yet a further object, feature, and/or advantage of the present invention to mimic the epithelial and mesenchymal stages and transitions from one to the other.

It is still yet a further object, feature, and/or advantage of the present invention to capture circulating tumor cells.

It is still yet a further object, feature, and/or advantage of the present invention to fit exosomes with a bioreactor.

It is still yet a further object, feature, and/or advantage of the present invention to obtain high throughput and high-quality data can be obtained with zero human risk.

It is still yet a further object, feature, and/or advantage of the present invention to allow administration and evaluation of efficacy of drugs or compounds under testing phases during drug discovery.

It is still yet a further object, feature, and/or advantage of the present invention to determine drug combinations and dosages for personalized medicine. Drug delivery systems including homing proteins and targeted drugs can be studied using this bioreactor.

It is still yet a further object, feature, and/or advantage of the present invention to extract and discover biomarkers.

It is still yet a further object, feature, and/or advantage of the present invention to facilitate an easier understanding cancer metastasis, design and test drugs, and drug delivery systems for cancer metastasis and develop diagnostic and interventional therapies for cancer metastasis.

The horizontal flow bioreactor disclosed herein can be used in a wide variety of applications. For example, examples are provided wherein aspects of the migration of prostate cancer and breast cancer cells are more easily quantified and/or analyzed.

It is preferred the apparatus be safe to operate, cost effective, stable, and able to reliably reproduce results.

Methods can be practiced which facilitate use, manufacture, assembly, maintenance, and repair of a horizontal flow bioreactor which accomplishes some or all of the previously stated objectives.

The horizontal flow bioreactor can be incorporated into systems, such as an incubator, which accomplish some or all of the previously stated objectives.

According to some aspects of the present disclosure, methods for modeling tumor growth and metastasis in vitro are provided. In certain embodiments, the methods comprise providing any of the horizontal flow bioreactors disclosed herein; introducing cells into the horizontal flow bioreactor; and flowing a medium through the horizontal flow bioreactor, wherein the flow mimics interstitial fluid flow conditions around the cells. In certain other embodiments, the methods comprise providing a horizontal flow bioreactor comprising a first bioreactor chamber; a second bioreactor chamber; a peristaltic pump that can regulate flow rate of a fluid; tubing for delivering the fluid between the pump, the first bioreactor chamber, the second bioreactor chamber; and an in-line injection port for sample insertion and/or sample extraction; introducing tumor cells into the horizontal flow bioreactor; and flowing a medium from the first bioreactor chamber to the second bioreactor chamber, wherein the flow mimics interstitial fluid flow conditions around the cells.

According to some other aspects of the present disclosure, methods for identifying a compound that inhibits tumor growth or metastasis are provided. The methods comprise providing a horizontal flow bioreactor comprising a first bioreactor chamber comprising a primary site scaffold seeded with tumor cells; a second bioreactor chamber comprising a secondary site scaffold; a peristaltic pump that can regulate flow rate of a fluid; tubing for delivering the fluid between the pump, the first bioreactor chamber, the second bioreactor chamber; and an in-line injection port for sample insertion and/or sample extraction; flowing a medium from the first bioreactor chamber to the second bioreactor chamber; introducing a test compound into the horizontal flow bioreactor; and assessing the efficacy of the test compound in inhibiting tumor growth or metastasis.

According to some additional aspects of the present disclosure, the test compound is assessed for an ability to inhibit the tumor cells from undergoing an epithelial to mesenchymal transition at the primary site scaffold, inhibit migration of the tumor cells from the primary site scaffold to the secondary site scaffold, inhibit attachment of circulating tumor cells to the secondary site scaffold, or inhibit the tumor cells from undergoing an epithelial to mesenchymal transition at the secondary site scaffold.

These and/or other objects, features, advantages, aspects, and/or embodiments will become apparent to those skilled in the art after reviewing the following brief and detailed descriptions of the drawings. Furthermore, the present disclosure encompasses aspects and/or embodiments not expressly disclosed but which can be understood from a reading of the present disclosure, including at least: (a) combinations of disclosed aspects and/or embodiments and/or (b) reasonable modifications not shown or described.

BRIEF DESCRIPTION OF THE DRAWINGS

Several embodiments in which the present invention can be practiced are illustrated and described in detail, wherein like reference characters represent like components throughout the several views. The drawings are presented for exemplary purposes and may not be to scale unless otherwise indicated.

An artisan of ordinary skill in the art need not view, within isolated figure(s), the near infinite number of distinct permutations of features described in the following detailed description to facilitate an understanding of the present invention.

DETAILED DESCRIPTION

The present disclosure is not to be limited to that described herein. Mechanical, electrical, chemical, biological, procedural, and/or other changes can be made without departing from the spirit and scope of the present invention. No features shown or described are essential to permit basic operation of the present invention unless otherwise indicated.

Figure 1:
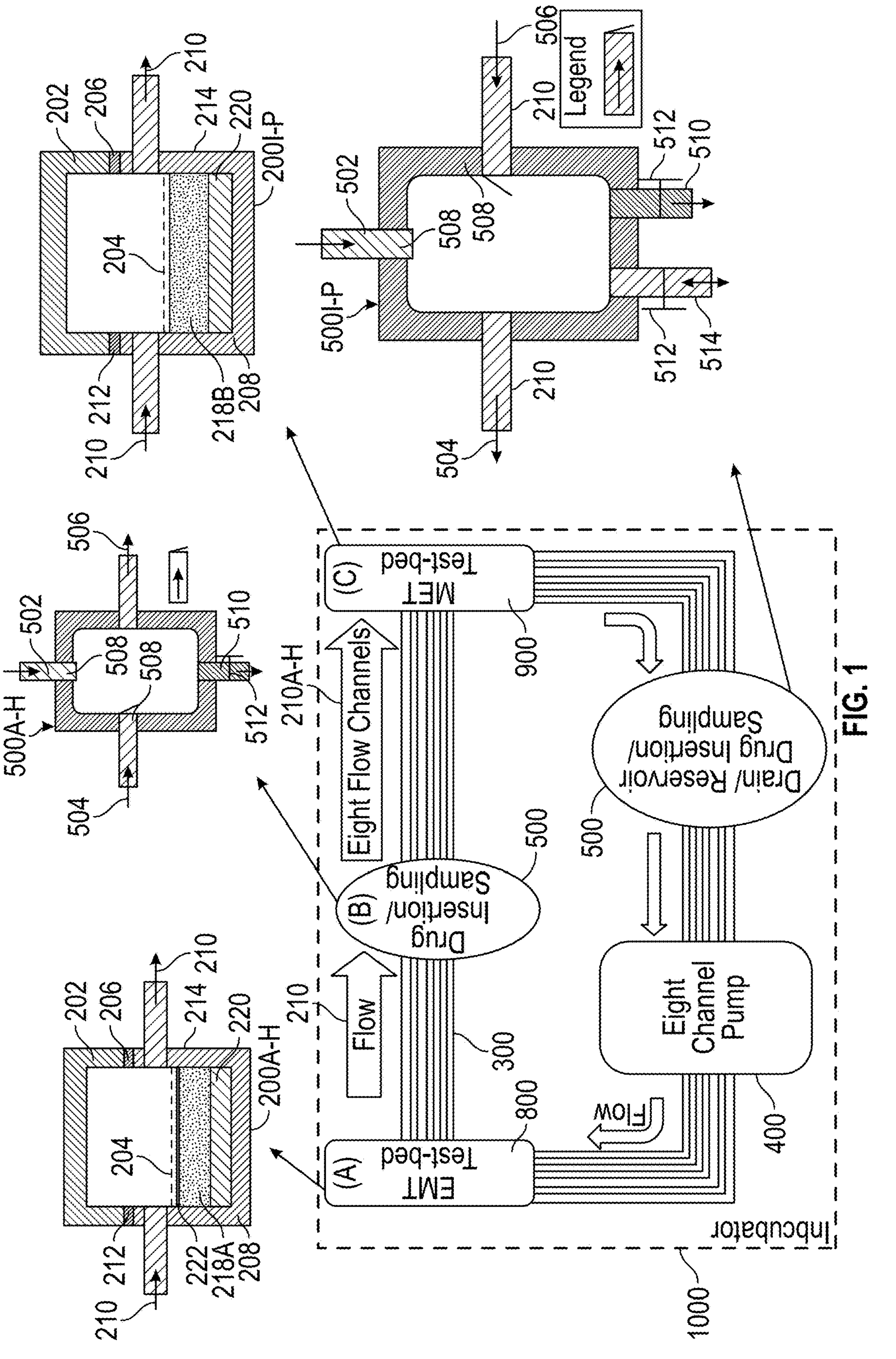
FIG. 1 shows a schematic of a horizontal flow EMT-MET metastasis scaffold flow reactor and a flow based integrated testing system for the evaluation of cancer progression device.
Figure 2:
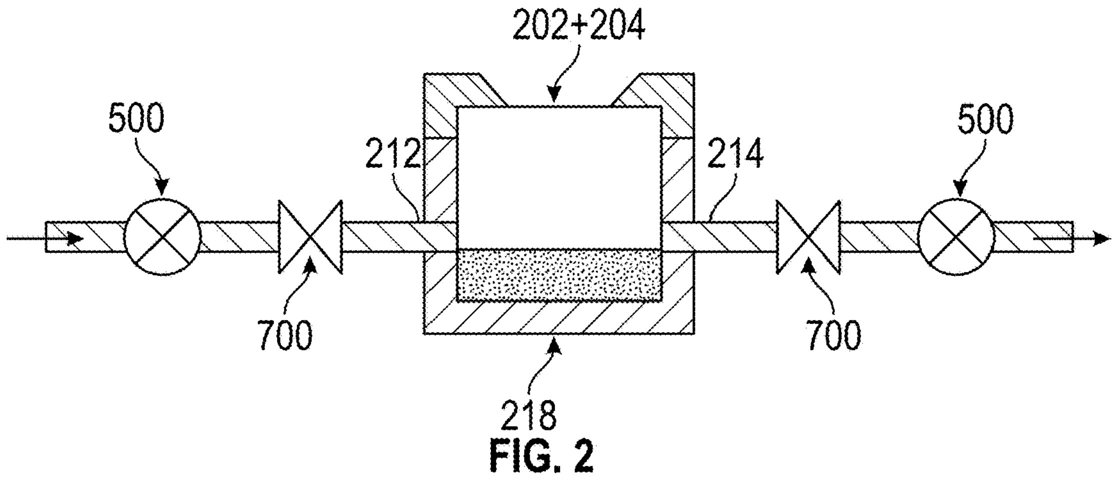
FIG. 2 shows a schematic representation of bioreactor setup and its components.

FIG. 1 shows a schematic of a horizontal flow EMT-MET metastasis scaffold flow reactor with an integrated testing system for the evaluation of cancer progression (FITS-CP). The horizontal flow bioreactor assembly 100 comprises one or more bioreactor chambers 200, tubing 300, a pump 400, ports 500, a fluid connection to media reservoirs 600, and quick connectors and disconnectors 700. In some embodiments, the bioreactor assembly 100 also includes the media reservoirs 600 themselves. The one or more bioreactor chambers are shown located at an EMT test-bed 800 and an MET testbed 900. The bioreactor can be placed within incubator 1000. A schematic representation of the bioreactor assembly 100 and its components are shown in FIG. 2. The bioreactor assembly 100 allows for the demonstration of the effects of dynamic conditions enabled with the horizontal flow bioreactor on prostate cancer viability and growth rate as compared to static culture.

Figure 3:
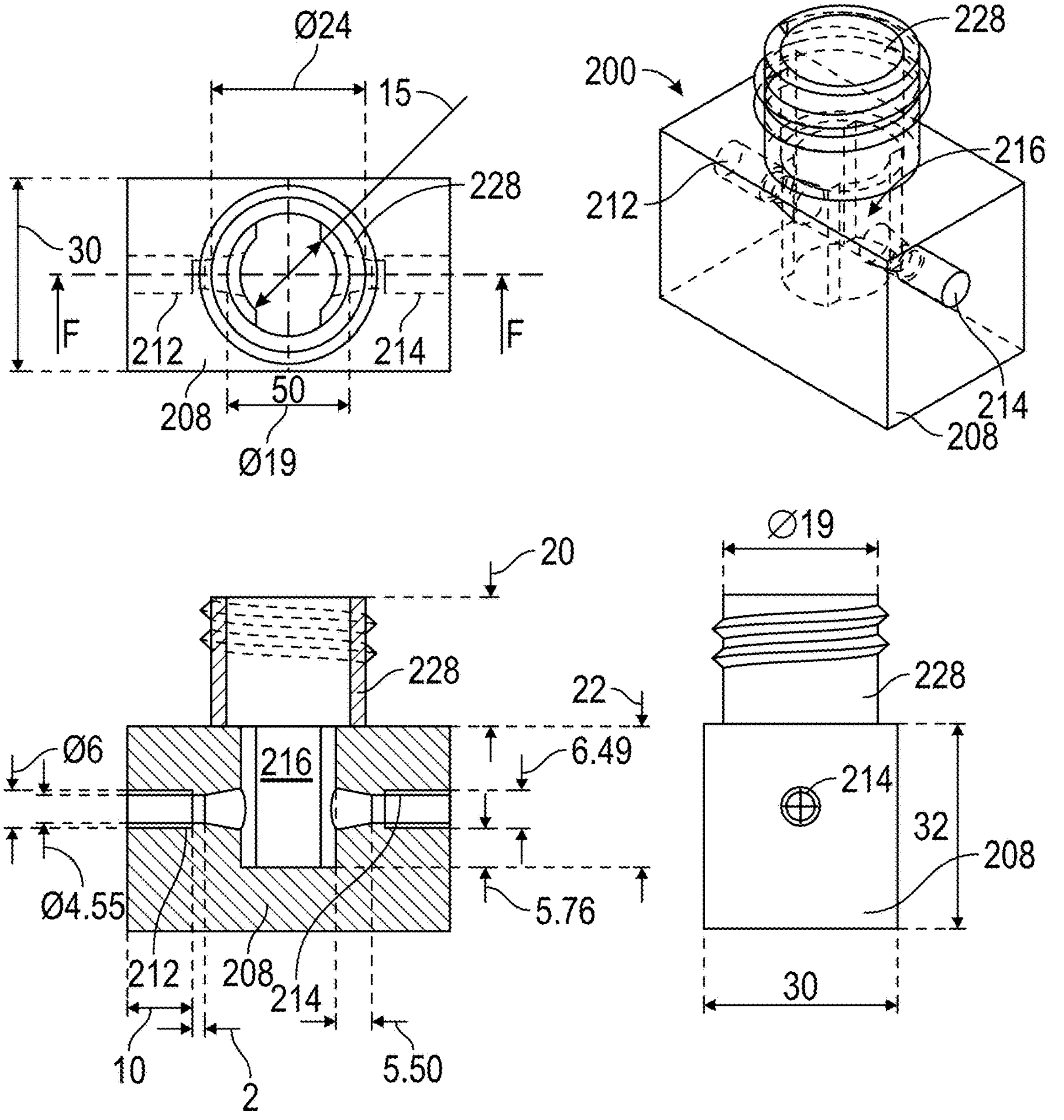
FIG. 3 shows a top plan view, a perspective view, a cross-sectional view, and a side elevation view of a bioreactor chamber.

The bioreactor chamber 200 shown in FIG. 3 hosts cell growth. Material selection for the bioreactor chamber 200 (also referred to as a culture chamber) is based on the component's biocompatibility and ability to be sterilized by the autoclaving process. However, in one embodiment, the bioreactor chamber 300 can be fabricated using a cross-linked polymethyl-methacrylate (PMMA) polymer. The bioreactor chamber 200 can be 3D-printed.

A vent cap 202 can cover to an upper opening that facilitates gas exchange within the culture chamber 200 and maintains a sterile environment for same. The vent cap 202 can include a porous membrane filter 204. Gaskets 206 can be employed to help secure said vent cap 202 to a well block 208 of the bioreactor chamber 200.

A horizontal flow 210 passes through the bioreactor chamber 200 by travelling along a fluid path defined by a horizontal flow channel. The horizontal flow channel receives fluid from a media inlet via inlet pore 212 and allows fluid to exit the bioreactor chamber 200 by way of a media outlet via outlet pore 214. Inlet and outlet pores 212, 214 are designed to accommodate barbed hose fittings. The hose fittings are further connected to silicone tubing 300 for continuous inflow and outflow of cell culture medium. The separate ports 500 are introduced on both sides of chambers 200 for cells and drug insertion into the inlet pore 212 and sample extraction from the outlet pore 214.

Space 216 making up the central portion of the chamber 200 can be, but is not limited to being, substantially rectangular. As shown, each culture chamber 200 has a corresponding scaffold 218. Scaffolds 218 can be employed both at the primary site (indicated by reference character 218A) and at a secondary site (indicated by reference character 218B) Cells grown on each scaffold 218 can be tested independently from other cell-seeded scaffolds. The scaffolds 218 can be raised and lowered by way of a variable height stage 220, wherein said stage 220 is vertically actuatable. A layer 222 of collagen and hydroxyapatite can be applied and/or form on an upper surface of the primary site scaffold 218A.

Figure 4:
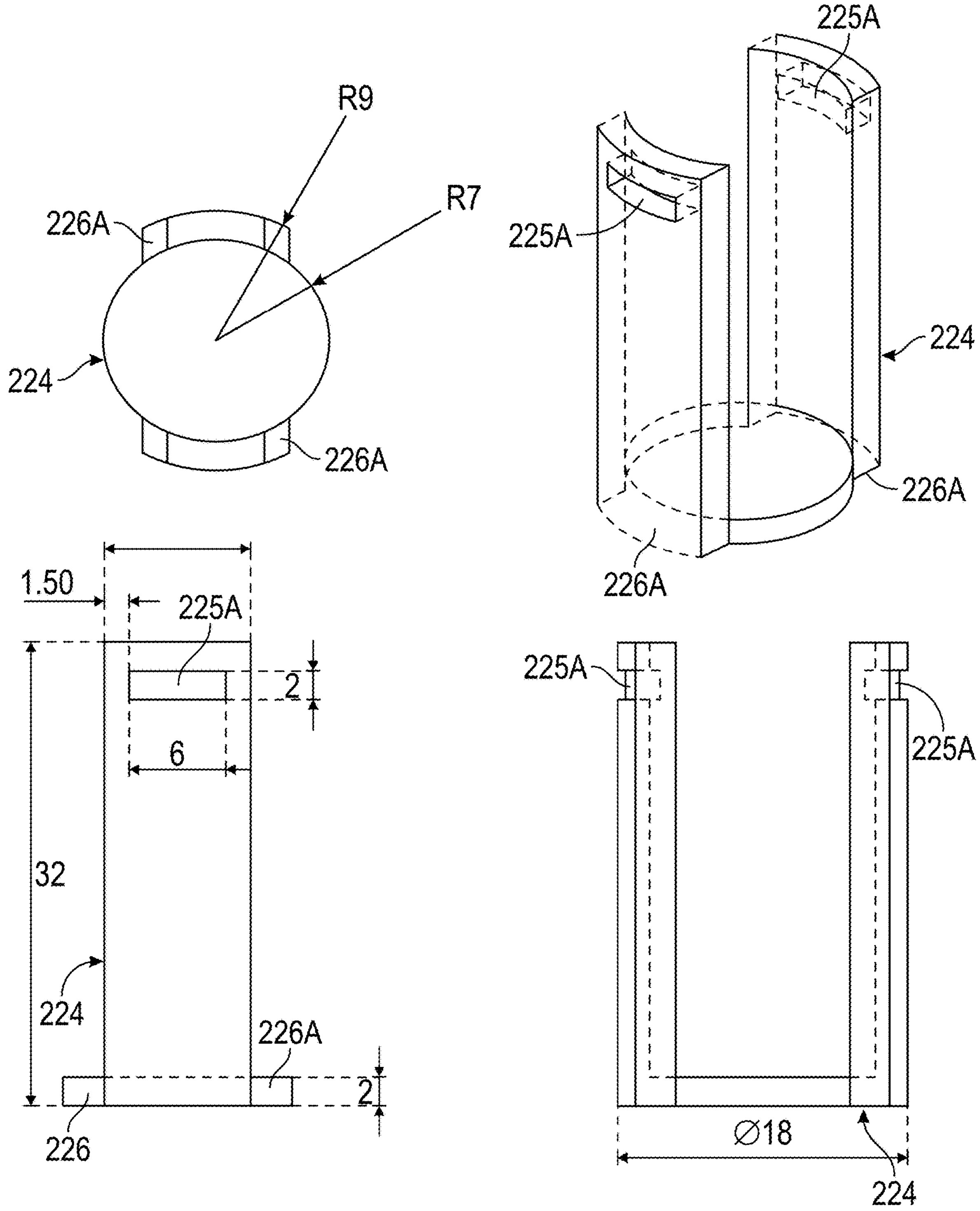
FIG. 4 shows a top plan view, a perspective view, a cross-sectional view, and a side elevation view of a scaffold holder.

Details of a scaffold holder 224 are shown in FIG. 4. The scaffold holder is a substantially resilient u-shaped member that can be inserted into the upper opening of the bioreactor chamber 200. In some embodiments, the scaffold holder 224 includes two notches 225A that allow for the scaffold holder to snap into place within the chamber 200 if aligned with corresponding, raised portions 225B of the chamber 200 and/or vent cap 202.

Figure 5:
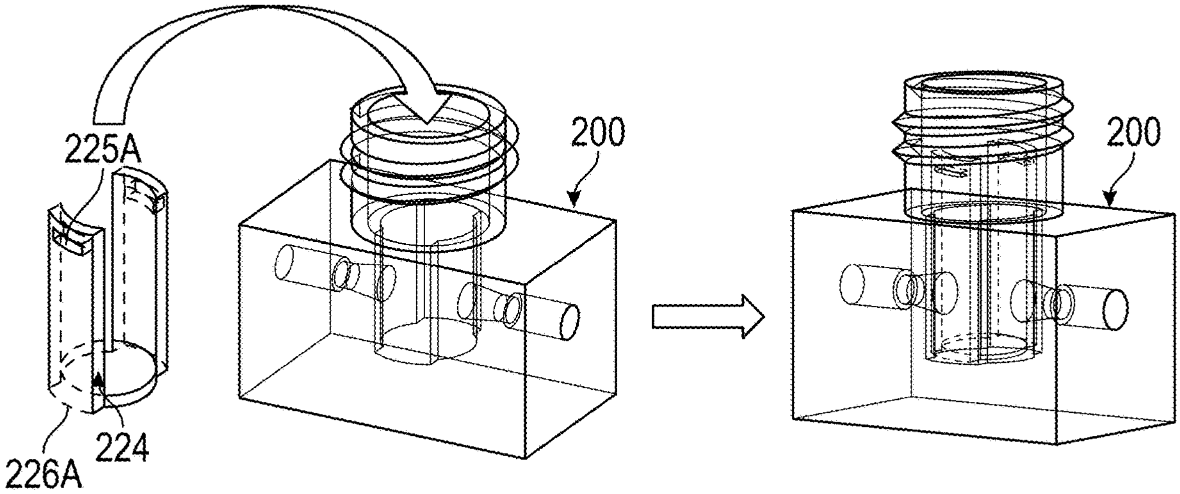
FIG. 5 shows a horizontal bioreactor assembly wherein the scaffold holder of FIG. 5 is inserted into bioreactor chamber of FIG. 3 with a vent cap eventually secured thereto.

The scaffold holder 220 is designed to put the scaffolds deep into the space 216 within the chambers 200 without flipping, as shown in FIG. 5. Insertion of the scaffold 218 into the rectangular space 216 can be further bolstered if there are arc-shaped spaces 226 on both sides of the scaffold 218 to keep the scaffold holder 224 immobilized.

As shown in FIG. 5, the vent cap 202 can tightened to the chamber 200 via threaded annular member 228 that protrudes from a base block 208. In a preferred embodiment, the annular member 228 includes the male threads and the vent cap 202 includes female threads located on an inner surface of same. Alternatively, it is to be appreciated the annular member 228 could also include female threads and the vent cap 202 includes male threads. In such a situation, the vent cap 202 would function more like a plug than a traditional cap.

Figure 6:
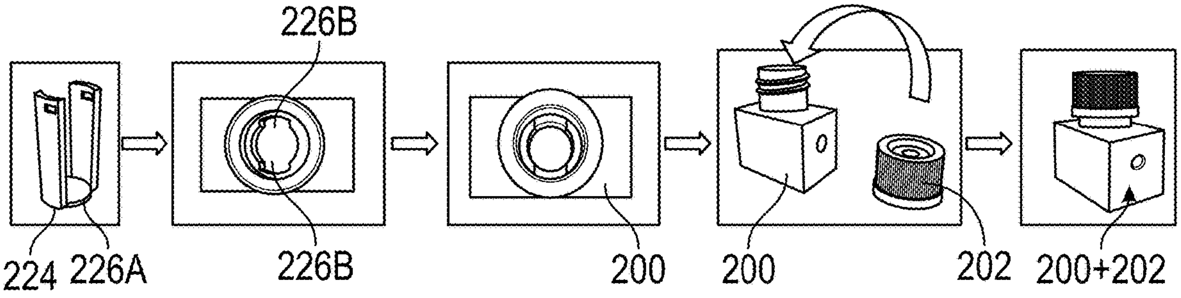
FIG. 6 shows a horizontal bioreactor assembly wherein transwell inserts are placed within the bioreactor chamber of FIG. 3.
Figure 6:
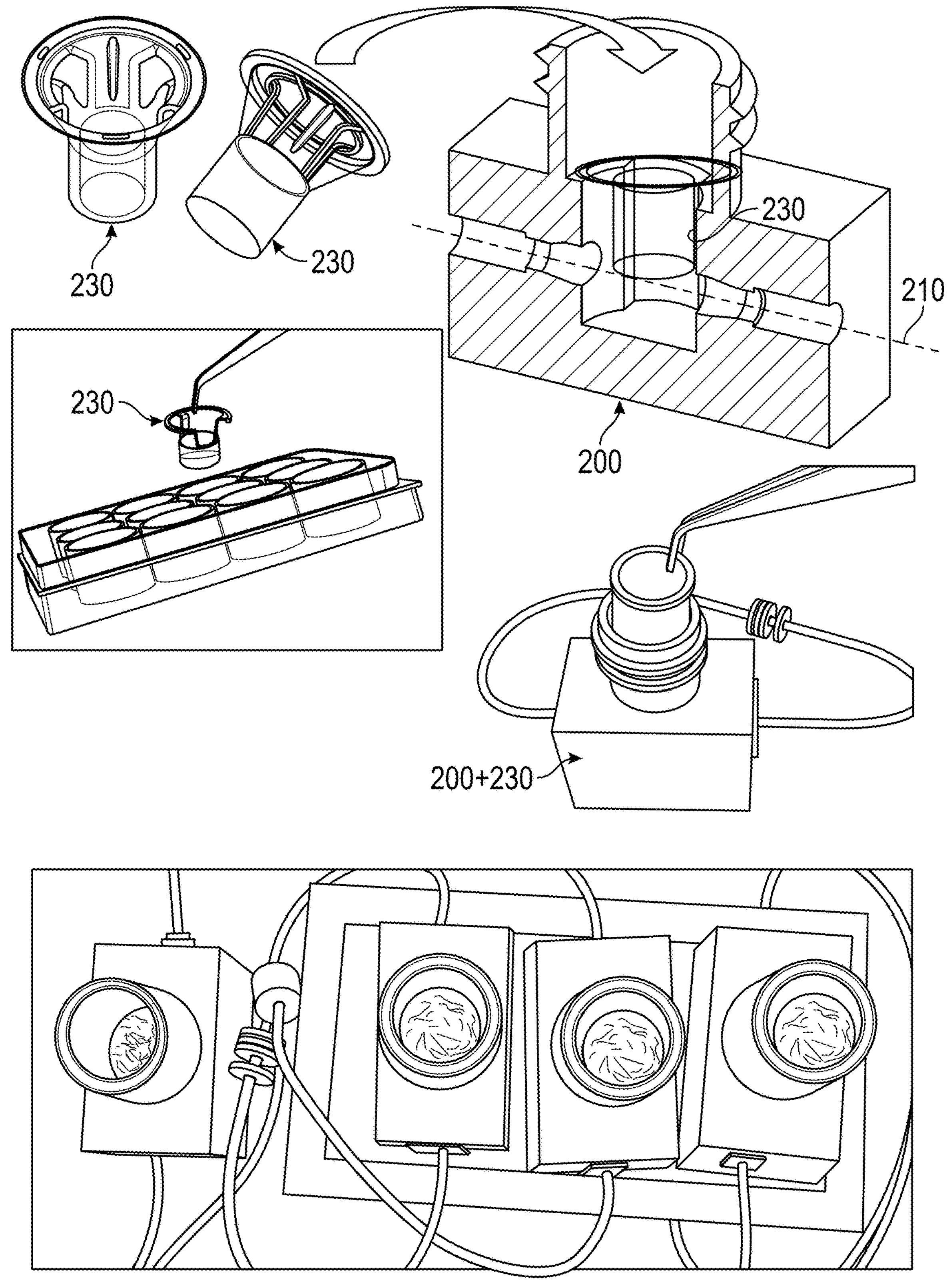
Figure 6:
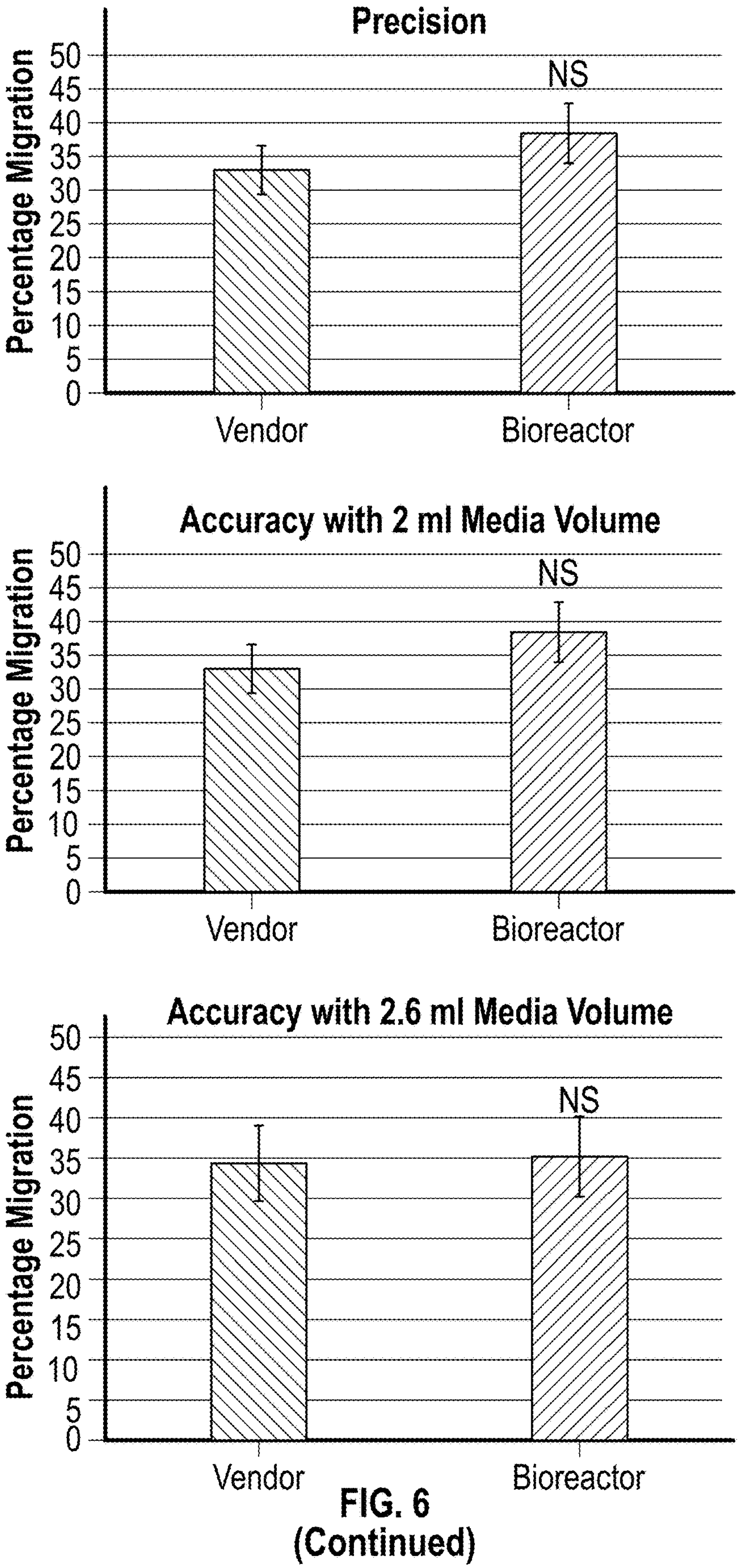

A porous transwell insert 230 can be used for the migration of cells in lieu of or in addition to use of the scaffold holder 220, as shown in FIG. 6. Use of a transwell insert 230 aides in understanding the role continuous fluid flow on the migration of said cells at their extravasation stage, where cancer cells start transmigrating from capillaries of distant organ to the tissue.

Figure 7:
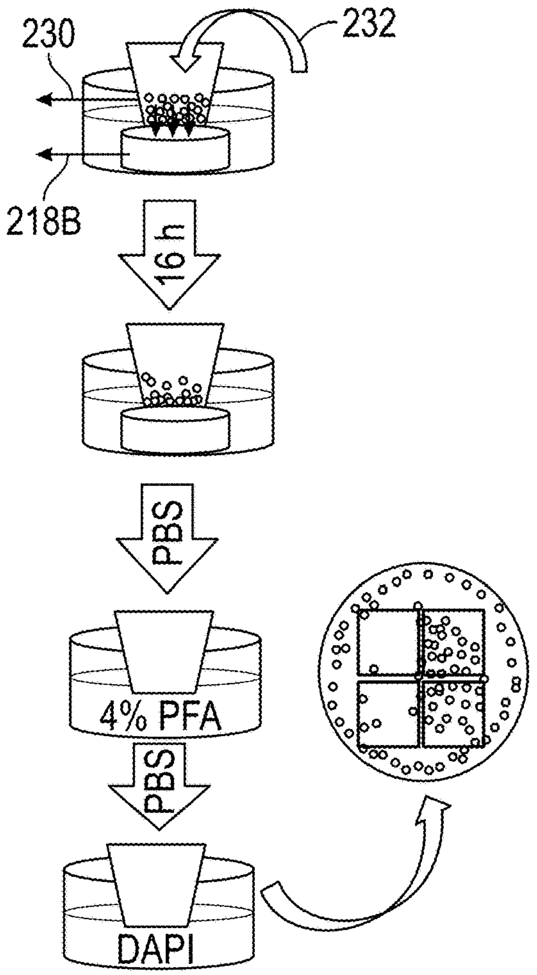
FIG. 7 shows a schematic view of a transwell migration assay procedure.

An example transwell migration assay procedure is shown in FIG. 7. To accommodate a transwell migration assay, the bioreactor assembly 100 can be customized to fit better the transwell insert 230 and a scaffold (e.g., a bone mimetic scaffold) 218B underneath the transwell insert 230. The procedure involves inserting the porous transwell insert 230 within the chamber 200, allowing cells within a serum-containing medium 232 to seed into said transwell insert 230, and allowing the cells to be adhered onto the scaffold 218B over time. Next, the media can be replaced with a serum (FBS) free media, and the inserts 230 were moved into the bioreactor 100. The cells migrate towards a primary location 218A on the transwell insert 230 containing media from the reservoir 600 toward the secondary location 218B. After incubation, cells that remained on top of the filter can be gently removed, such as through the use of cotton swabs. The percentage of cells migrated through the filter can be measured using a reagent assay.

In some embodiments, the tubing 300 comprises peroxide cured silicone. The tubing 300 delivers fluid between the pump 400, the chambers 200, and the media reservoirs 600. The tubing 300 can be, but is not required to be, approximately one sixteenth of an inch (1/16").

The pump 400 can be a peristaltic pump for regulating the flow rate of the fluid. The peristaltic pump can include have a digital user-interface. The pump 400 is preferably a multi-channel pump. In the embodiment shown in FIG. 1, the pump 400 pumps fluid for eight channels 210A-H, and there are eight bioreactor chambers 200A-H in the EMT test-bed 800 that correspond with the eight channels 200A-H, eight insertion ports 500A-H for inserting samples, bioreactor chambers 200I-P at the MET test-bed 900, and eight extraction ports 500I-P for extracting samples. It is however to be appreciated that any number of flow channels 210, bioreactor chambers 200, and insertion ports 500 can be used.

The ports 500 are in-line with the horizontal flow(s) 210. Some of the ports 500 are insertion ports and can be utilized for inserting drugs and/or samples into the flow 210. If the port 500 is an insertion port, the port 500 can include an upper drug insertion port 502 connected to a syringe pump, a first channel 504 to the EMT test-bed 800, a second channel 506 from the MET test-bed 900, one-way check flow valve(s) 508, a sample extraction port 510, and shut off valve(s) 512. If the port 500 is intended to be used as a drain, the port 500 can include an upper drug insertion port 502 connected to a syringe pump, a first channel 504 from the EMT test-bed 800, a second channel 506 to the MET test-bed 900, one-way check flow valve(s) 508, a sample extraction port 510, shut off valve(s) 512, and drain(s) 514. The first channel 504 and the second channel 506 are preferably in-line.

In some embodiments, the media reservoirs 600 comprise borosilicate glass bottles. The media reservoirs in some embodiments have a capacity between half a liter (0.5 L) and one and one-half liters (1.5 L), in other embodiments will have a capacity between two hundred fifty millimeters (250 mL) and seven hundred fifty milliliters (mL), and in still other embodiments have a capacity between fifty milliliters (50 mL) and one hundred fifty milliliters (150 mL).

The quick connectors and disconnectors 700 can include barbed fittings and/or Luer locks to connect the tubing 300 to various components. The barbed fittings and/or Luer locks are sized to correspond with an outer diameter of said tubing 300.

Figure 8:
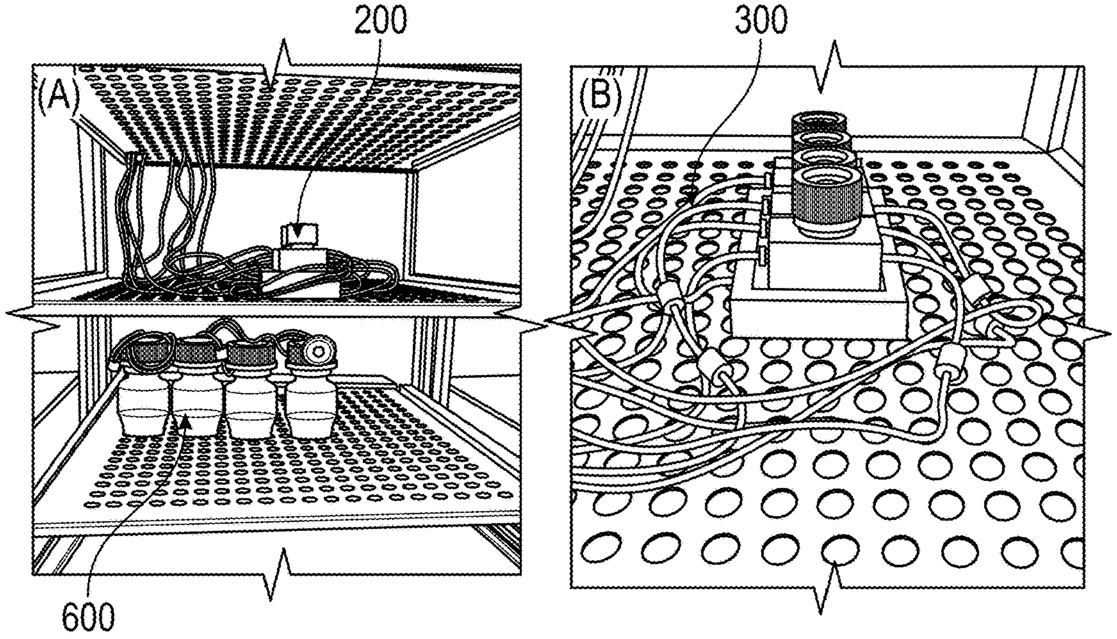
FIG. 8 shows a bioreactor assembly inside an incubator, wherein bioreactor chambers are located toward the top and media bottles at the bottom of the incubator.

As mentioned above, the bioreactor assembly(ies) 100 can be placed within an incubator 1000, as shown in FIG. 8.

Cell Culture

The cancer cell can be any cancer cell. For example, the cancer cell can be a breast cancer cell, a large intestinal cancer cell, a lung cancer cell, a small cell lung cancer cell, a stomach cancer cell, a liver cancer cell, a blood cancer cell, a bone cancer cell, a pancreatic cancer cell, a skin cancer cell, a head or neck cancer cell, a cutaneous or intraocular melanoma cell, a uterine sarcoma cell, an ovarian cancer cell, a rectal or colorectal cancer cell, an anal cancer cell, a colon cancer cell, a fallopian tube carcinoma cell, an endometrial carcinoma cell, a cervical cancer cell, a vulval cancer cell, a vaginal carcinoma cell, a Hodgkin's disease cell, a non-Hodgkin's lymphoma cell, an esophageal cancer cell, a small intestine cancer cell, an endocrine cancer cell, a thyroid cancer cell, a parathyroid cancer cell, an adrenal cancer cell, a soft tissue tumor cell, an urethral cancer cell, a penile cancer cell, a prostate cancer cell, a chronic or acute leukemia cell, a lymphocytic lymphoma cell, a bladder cancer cell, a kidney cancer cell, a ureter cancer cell, a renal cell carcinoma cell, a renal pelvic carcinoma cell, a CNS tumor cell, a primary CNS lymphoma cell, a bone marrow tumor cell, a brain stem nerve gliomas cell, a pituitary adenoma cell, a testicular cancer cell, an oral cancer cell, a pharyngeal cancer cell, or a uveal melanoma cell.

In certain embodiments, the cancer cells are prostate cancer cells. PC3 prostate cancer cells are commercially αvailable. Cells can then be cultured within the media reservoirs 600 and maintained under standard culture conditions (e.g., 5% CO2 at 37° C. with high moisture). A bicarbonate, 10% fetal bovine serum ("FBS"), and a 1% Penicillin-Streptomycin antibiotic solution can then be formed.

Scaffolds

The scaffolds 218 prepared can be polycaprolactone/in situ hydroxyapatite nanoclay based ("PCL/in situ HAPclay") scaffolds. A modified montmorillonite (MMT) clay with 5-aminovaleric acid can be applied to the scaffolds to increase the d-spacing of nanoclay sheets. HAP can be introduced into intercalated nanoclay galleries to make in situ HAPclay. Further, PCL and 10% in situ HAPclay can be dissolved in 1, 4-dioxane to obtain a composite mixture subjected to freeze-extraction to make in situ HAPclay scaffolds. The PCL/in situ HAPclay scaffolds mimic bone.

The secondary site scaffolds can be organ specific. In certain embodiments, the secondary site scaffold is a bone mimetic scaffold, a lung mimetic scaffold, a liver mimetic scaffold, or a brain mimetic scaffold.

Cell Seeding

The scaffolds 218 can be sterilized under ultraviolet (UV) light for a sufficient time period (e.g., about 1 hour) and then immersed the scaffolds into an ethanol solution (e.g., approximately 70% ethanol solution) for an extended period of time (e.g., about 12 hours). The scaffolds 218 can be washed with 1× phosphate buffer saline (PBS). After cell seeding, the scaffolds 218 can be incubated within incubator 1000 at standard culture conditions for 1 day as a control. Next, four scaffolds 218 can be transferred into four different bioreactor chambers 200, which are arranged in fluid parallel. Additional scaffolds 218 can be cultured in static conditions for comparing data.

Bioreactor Setup

The bioreactor chambers 200 and media bottles 600 were placed inside the incubator 1000 at standard culture conditions, as shown in FIG. 8. Culture medium can be added in each media bottle 600. A continuous flow rate (e.g., 0.05 ml/min, 0.2 ml/min) can then be maintained.

Injection Ports+Stirrer

Figure 9:
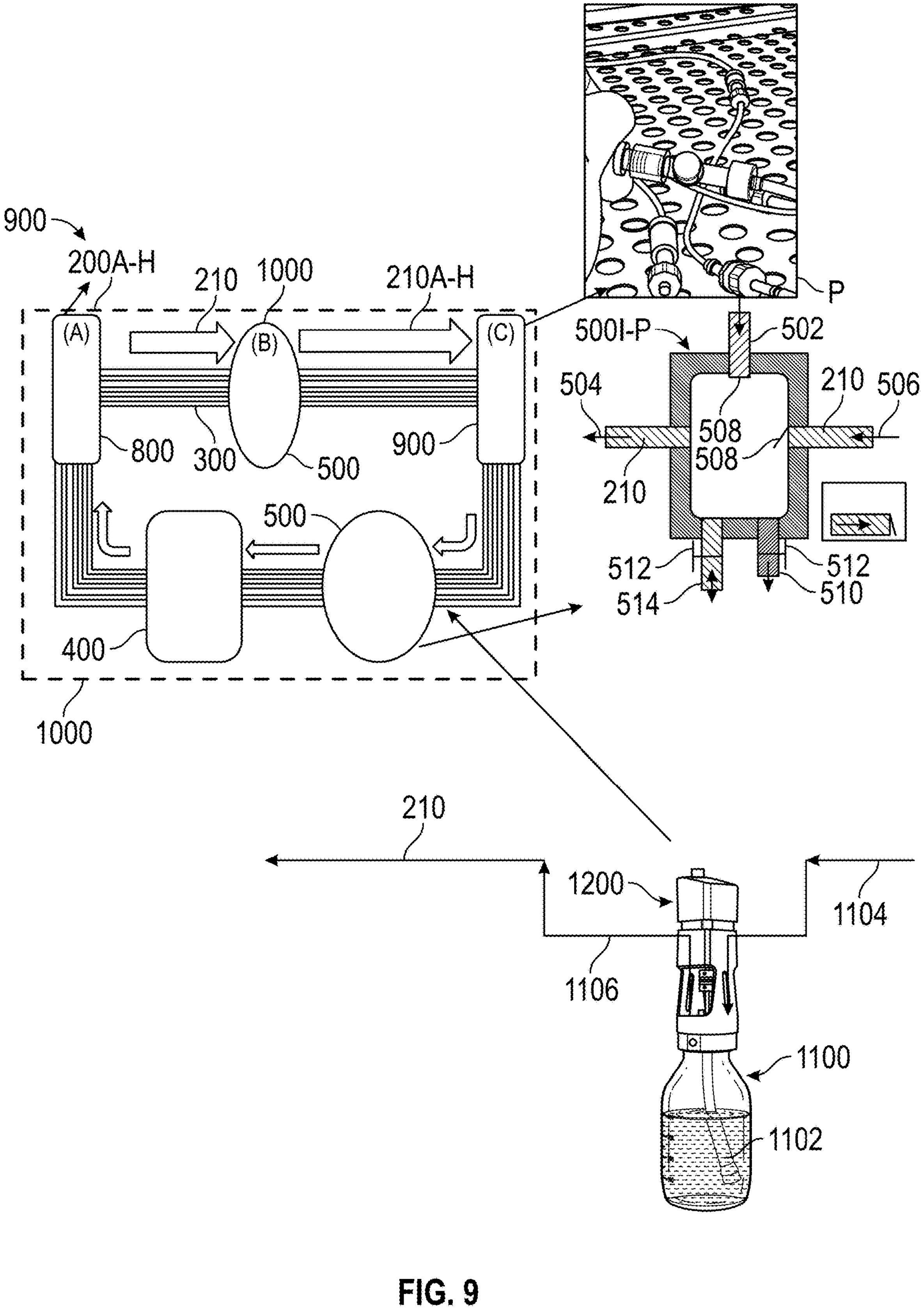
FIG. 9 shows another schematic of a horizontal flow EMT-MET metastasis scaffold flow reactor and a flow based integrated testing system for the evaluation of cancer progression device.

In another embodiment of FIG. 9, a bioreactor model 900 having the components shown and described with the bioreactor model 100 is further improved for its application based on the addition of injection ports 1000 and a stirrer 1100 powered by a motor 1200.

Figure 10:
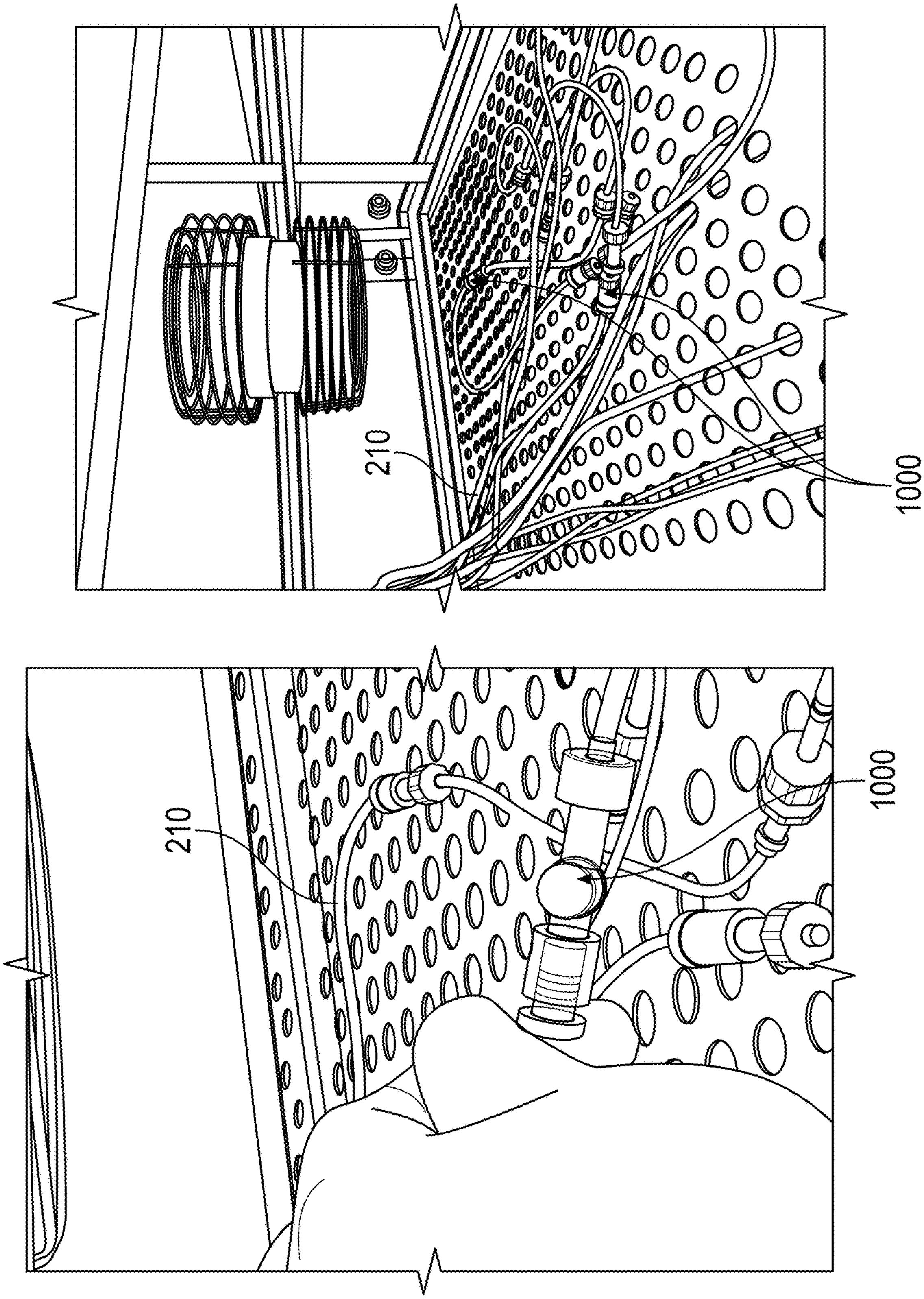
FIG. 10 shows

For example, in FIG. 10, injection ports 1000 are added to each flow channel 210 to allow insertion of cells into the flow. Same ports can be used to insert drugs or other chemicals and can be used for extracting samples including circulating cells from the flow without interrupting the flow.

Figure 11:
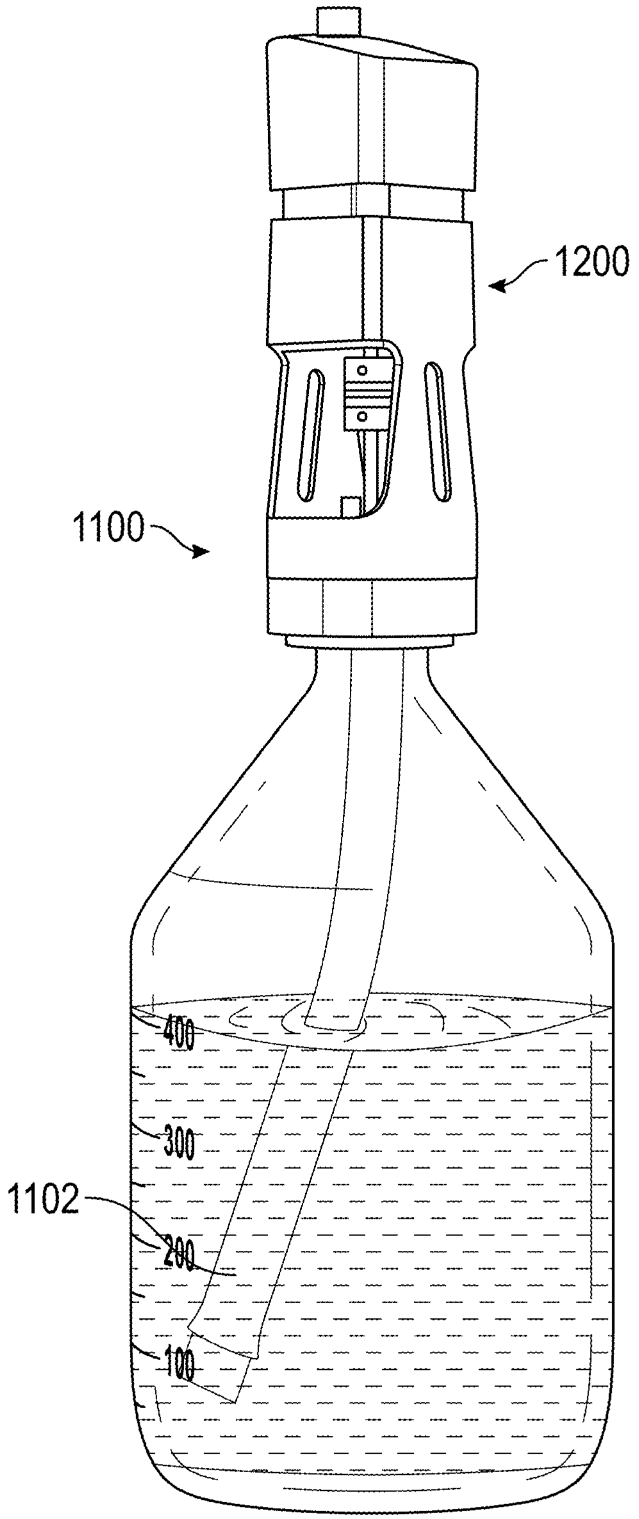
FIG. 11 shows a detailed view of a stirrer to prevent circulating cells from settling down in the reservoir.

FIG. 11 shows a stirrer 1100 that prevent circulating cells in the flow from settling down in the reservoir. In a preferred embodiment, there is one stirrer 1100 per flow channel 210. The stirrer is an agitator that can put flow that comes in 1104 into motion by shaking or stirring to change a fluidic characteristic of flow that goes out 1106.

Figure 12:
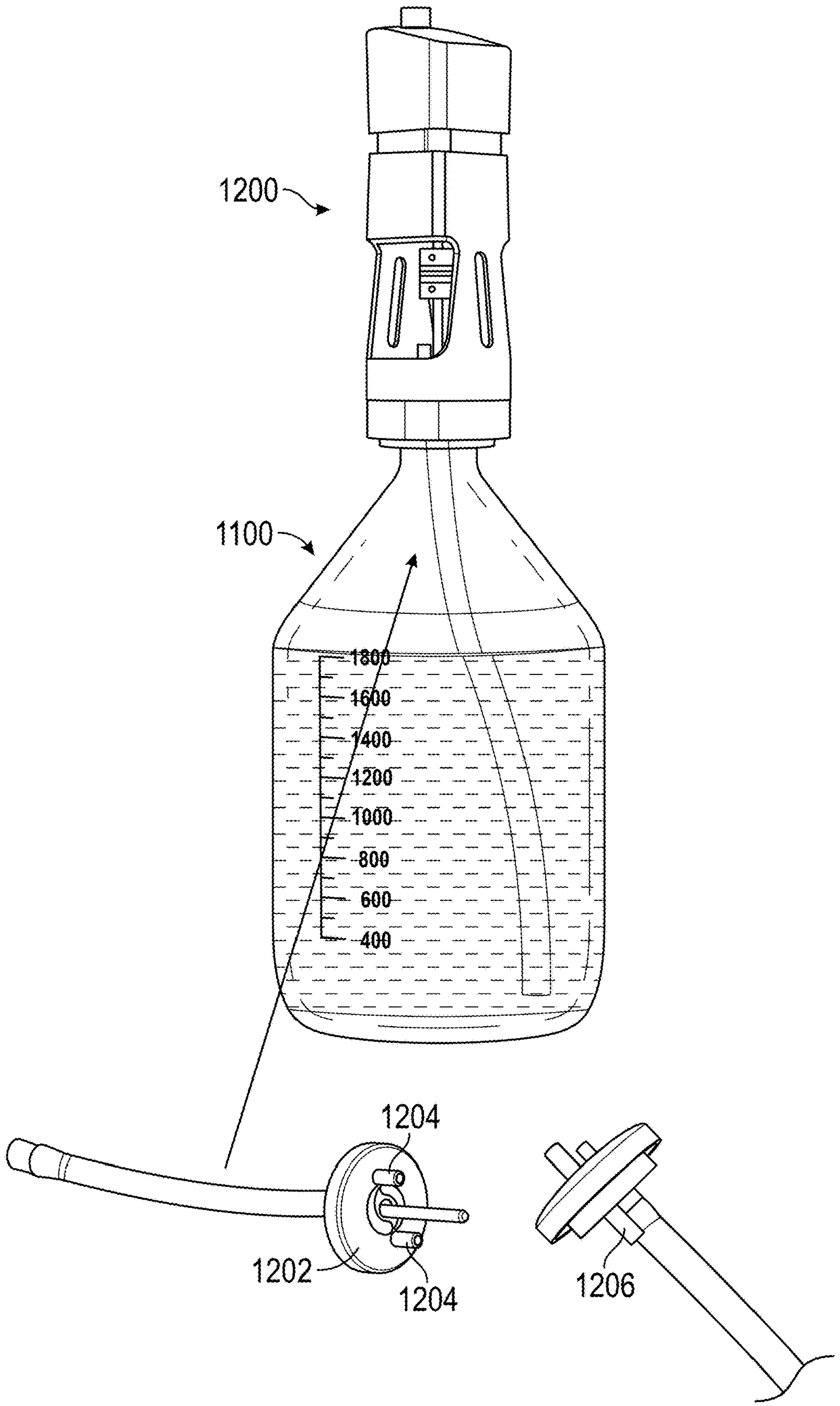
FIG. 12 shows a detailed, exploded view of the stirrer of FIG. 11 and some of its internal components.

In general, agitators usually consist of a motor powered impeller 1200 and a shaft 1102. The impeller is the rotor 1200 located within a tube or conduit attached to the shaft 1102. Pressure can be enhanced for the flow of a fluid to be done. Process control can be used to maintain better control over the mixing process. A lid 1202 separates the shaft 1102 form the motor powered impeller 1200 and two outside ports 1204 and an inside port 1202, as shown in FIG. 12.

Live-Dead Assay

To evaluate the cell viability qualitatively, a live-dead assay can be performed on one sample each from the control, one of the scaffolds 218 in static conditions after a certain amount of time (e.g., 4 days), and dynamic conditions after said certain time. The scaffolds 218 can be washed with PBS and incubated them in a staining solution for less than an hour at room temperature in the dark. Images can then be taken of the scaffolds 218 using a confocal microscope.

Proliferation Assay

To determine the proliferation of cells quantitatively, an Alamar Blue cell proliferation assay can be performed. After choosing scaffolds 218 from the dynamic and static culturing conditions, the scaffolds 218 can be washed with PBS and incubated with an Alamar Blue solution at standard culture conditions for approximately three hours. Fluorescence can be measured at a plurality of distinct emission wavelengths using a fluorescence microplate reader. Cells seeded in the wells without inserts can be used as a positive control. As a negative control, an Alamar Blue solution can be to the wells without cells. Fluorescence emitted only by an Alamar Blue reagent can thus be considered a background signal. The percentage migration can be calculated by using the formula:

$$\text{Percentage migration} = \frac{\text{Fluorescence of migrated cells} - \text{background signal}}{\text{Fluorescence of total cells without insert} - \text{background signal}} \times 100$$

Statistical Analysis

Statistical analysis can be carried out using software in triplicates (n=3) and the data are presented as mean±standard derivation. A p-value of less than 0.05 can be considered significant. The statistical significance between groups can be determined using the Student's T-test.

It is to be appreciated the bioreactor model 100 and the transwell insert 224 can be designed using computer-aided design (CAD) software. The theoretical analysis of the hydrodynamic performance of the bioreactor can thus be conducted by computational fluid dynamics (CFD), using a flow simulation package. For example, SolidWorks Flow Simulation is a CAD-integrated Computational Fluid Dynamics (CFD) simulation software fully integrated with the part design environment. SolidWorks Flow and other Cartesian meshing approaches can be integrated directly into a native CAD system and used with a discrete numerical technique based on the Finite Volume Method (FVM) to integrate with CFD solvers. The fluid medium in the bioreactor can, by way of example, be assumed to be an incompressible fluid. The scaffold geometry can also be approximately and improved heuristically after many iterations of experimentation. Inlet flow rates can also be based upon statistical analysis and experiments performed.

Methods of Using the Horizontal Flow Bioreactors

Methods for modeling tumor growth and metastasis in vitro are provided.

Figure 13:
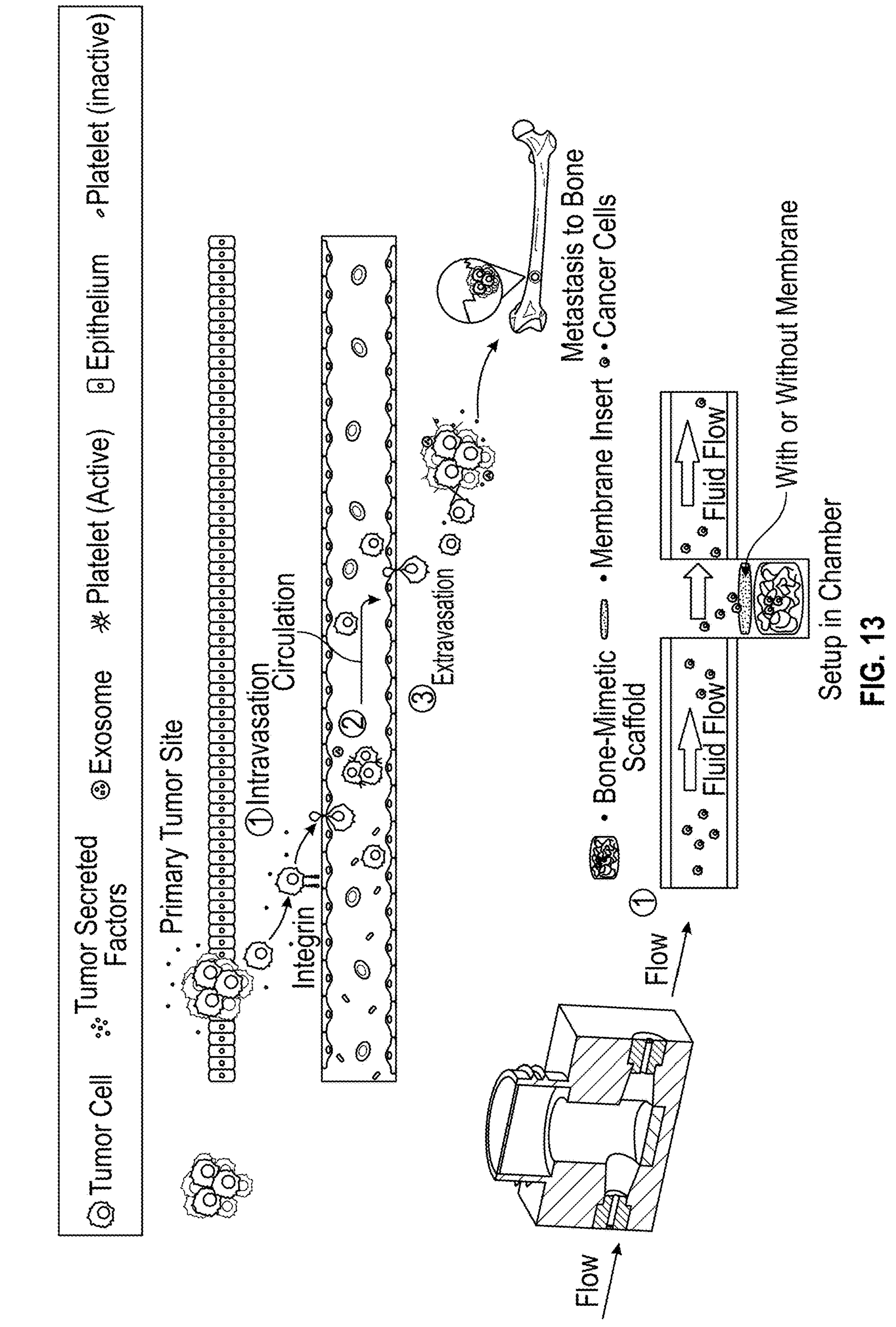
FIG. 13 shows a horizontal bioreactor experimental plan to simulate circulating cancer cells extravasation to bone.
Figure 14A:
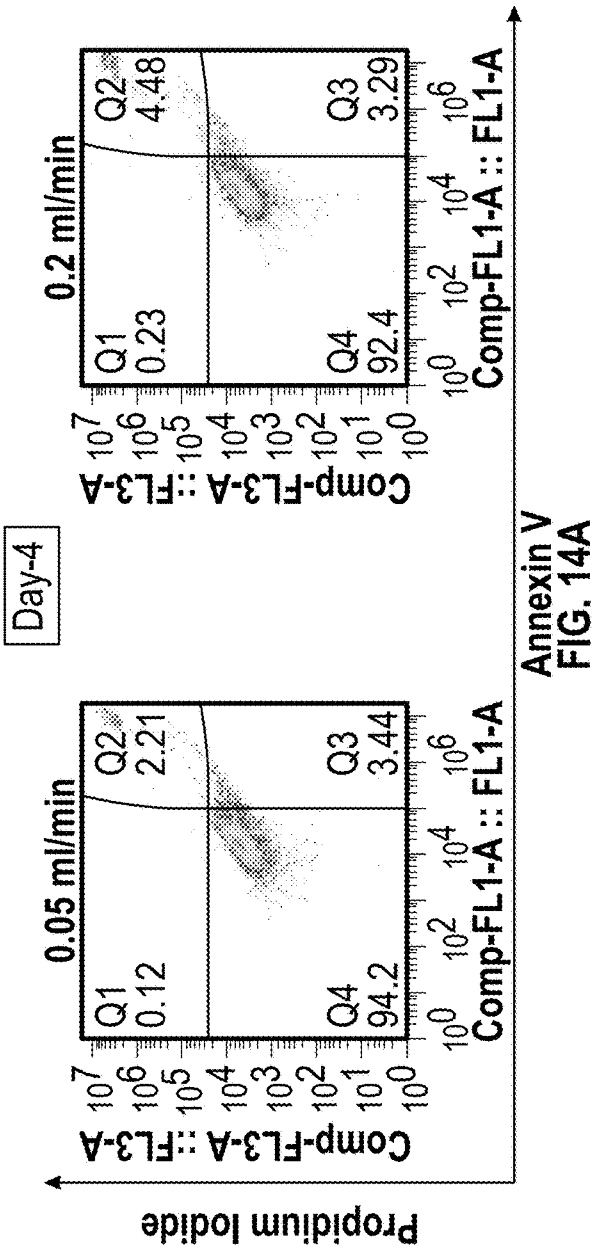
FIGS. 14A-14G show cell apoptosis assays. 14A, 14B, and 14G: cell apoptosis assessed at 0.05 ml/min and 0.2 ml/min flow rates, with a representative dot plot presenting percent live, early, and late apoptotic cells following double staining with Annexin V and Propidium Iodide on Day-4 (14A and 14G) and Day-8 (14B and 14G). 14C and 14E: The bar graphs show the percentage of cell apoptosis was calculated on Day-4 and Day-8 by adding percentage early apoptotic and late apoptotic cells under different conditions (14C) and quantitative RT-PCR data for apoptosis-related genes on Day-8 (14E). 14D and 14F: Also shown in a schematic view of a possible mechanism of TGF-β1 mediated tumor suppression and tumor induction (14D) and images capturing protein expression of p-Smad2 and p-Akt assessed by western blotting on Day-8 (14F).
Figure 14B:
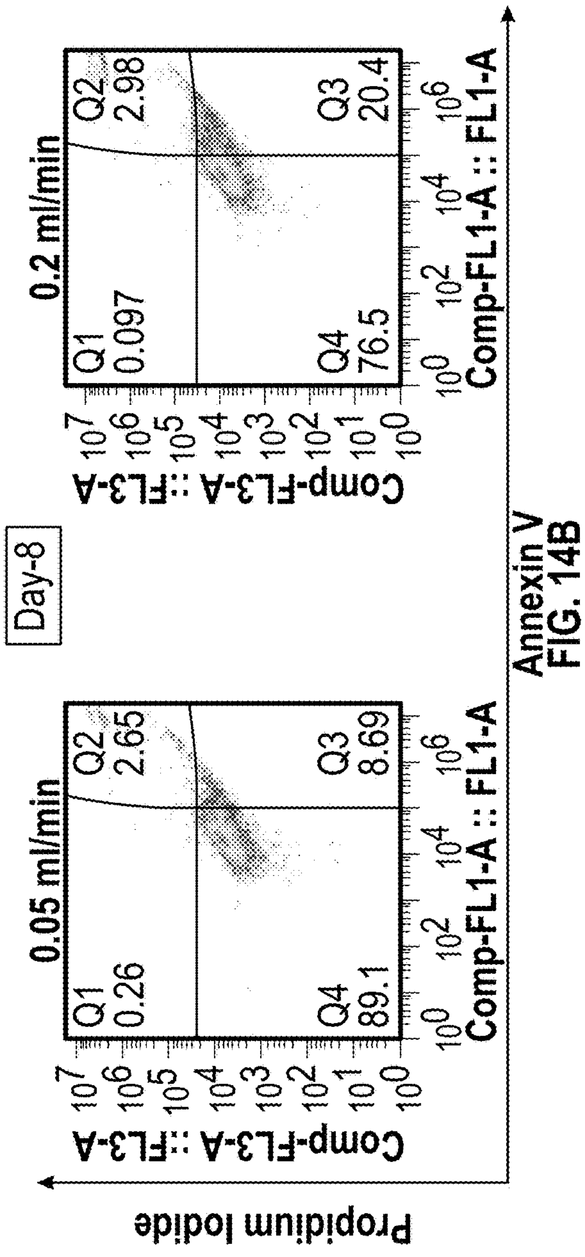
Figure 14D:
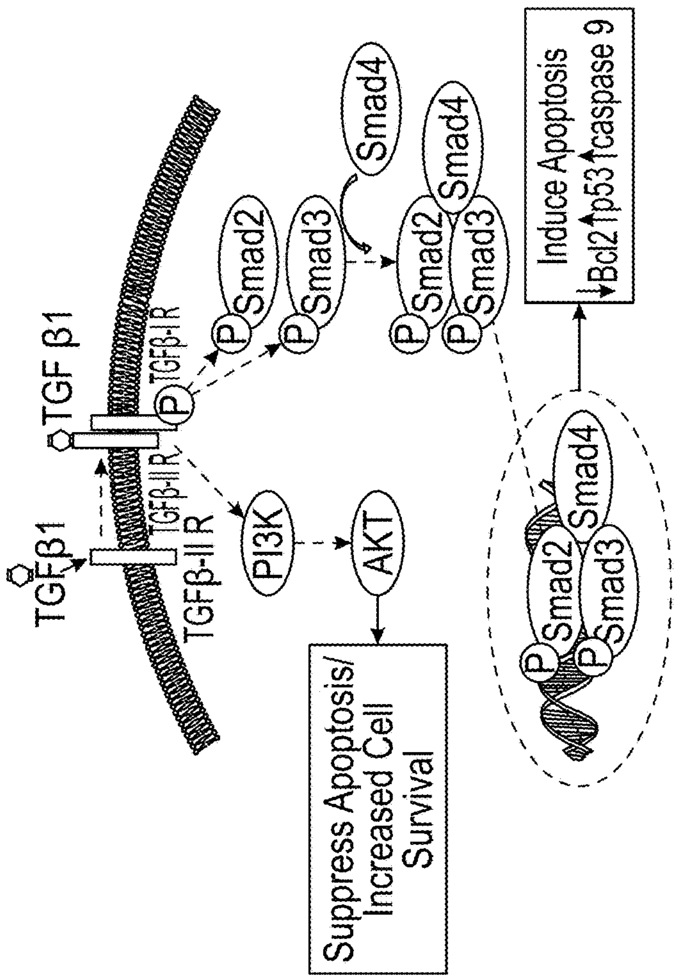
Figure 14F:
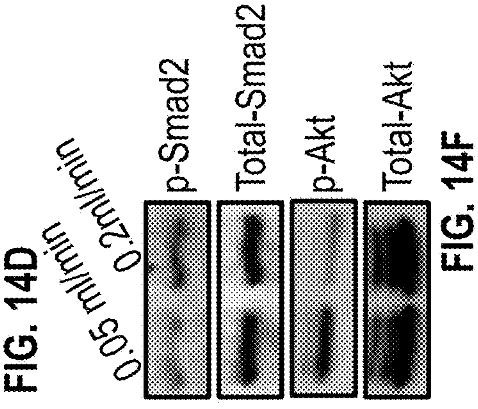
Figure 14C:
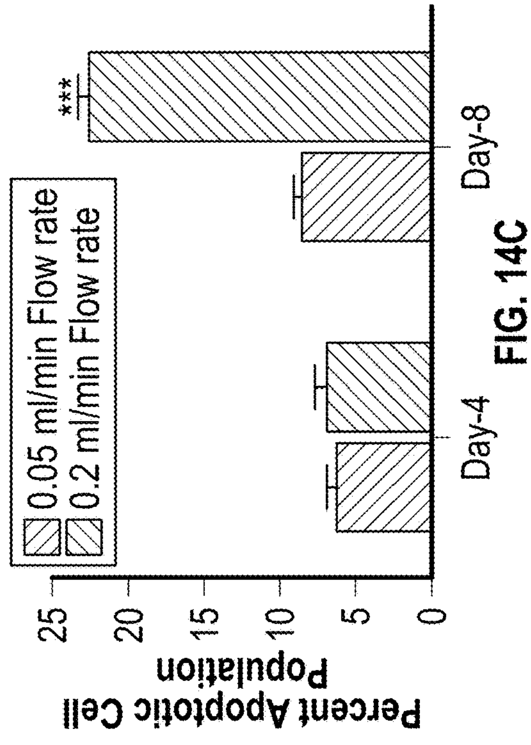
Figure 14E:
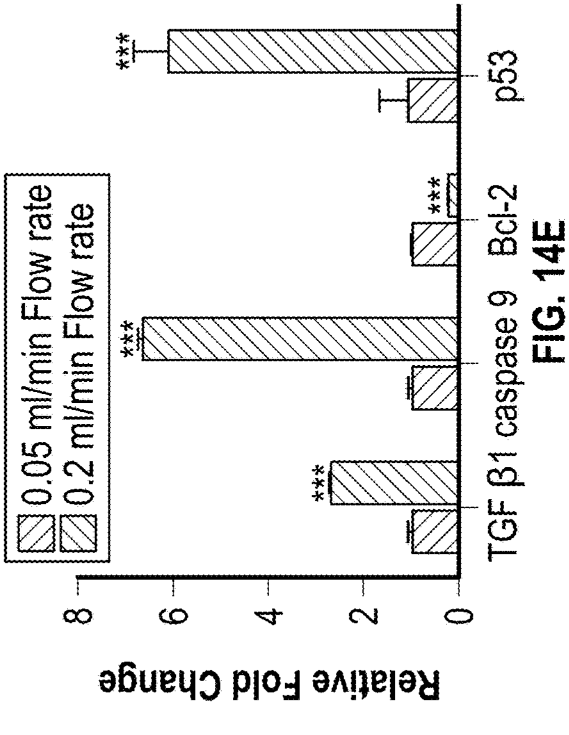
Figure 14G:
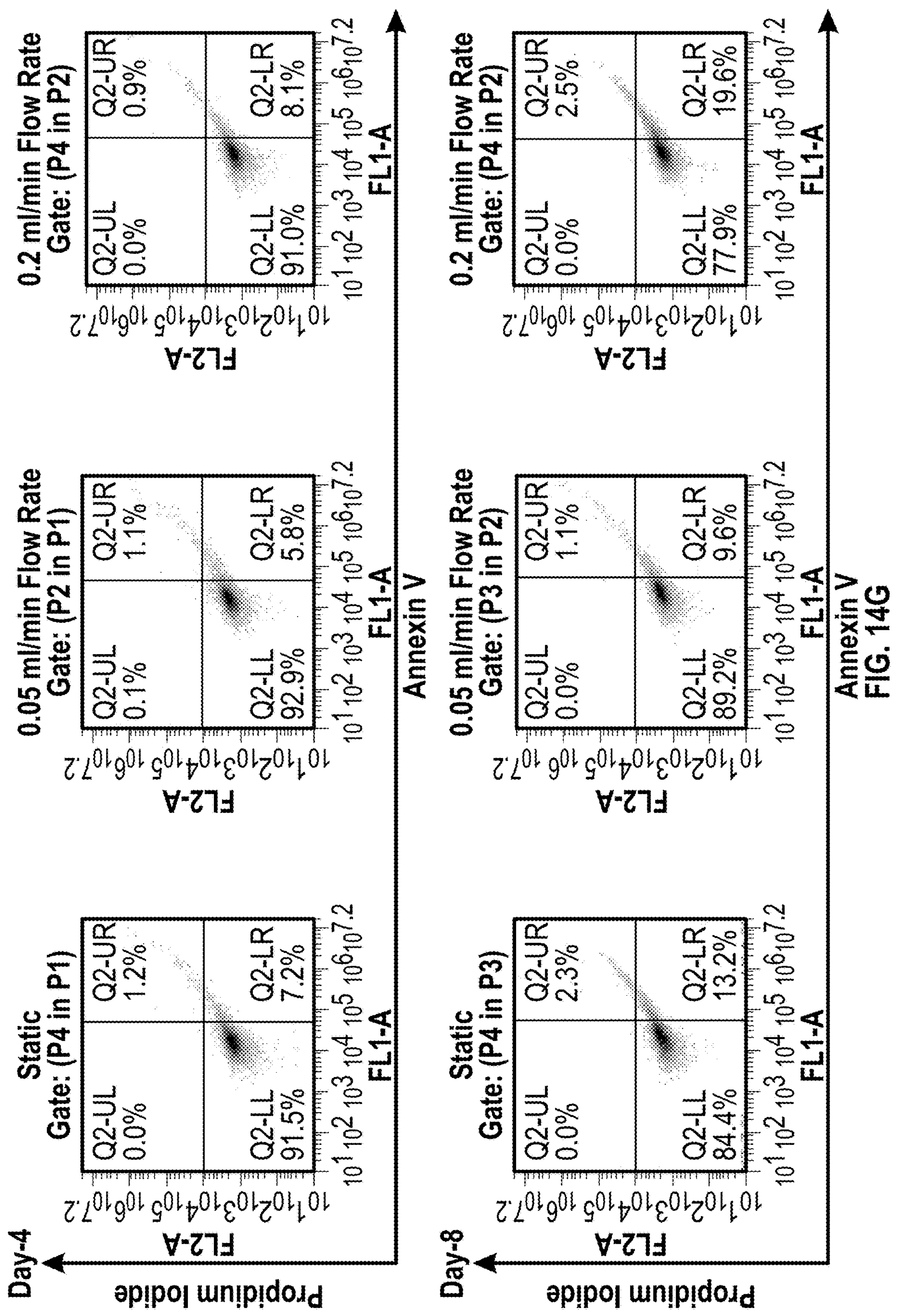

For example, FIG. 13 shows schematics for a horizontal bioreactor experimental plan to simulate circulating cancer cells extravasation to bone.

Cancer progression goes through two important phases; the first being epithelial to mesenchymal transition ("EMT") of cancer cells followed by mesenchymal to epithelial transition ("MET") that occurs at metastasis. The horizontal flow bioreactors can mimic both stages and also the transition of one to the other.

The term "epithelial-to-mesenchymal transition" ("EMT") is known in the art and refers to a process whereby epithelial cells take on a mesenchymal phenotype. Cells that have undergone EMT display properties of a mesenchymal cell, such as increased migratory and invasive ability (e.g., pro-metastatic properties), self-renewal capacity, tumorigenicity, increased resistance to chemotherapeutic agents, increased expression of biomarkers associated with the mesenchymal state, and decreased expression of biomarkers associated with the epithelial state. The term "mesenchymal-to-epithelial transition" ("MET") is also known in the art and refers to the reprogramming of cells that have undergone EMT to regain one or more epithelial characteristics.

Examples of characteristics of epithelial cells or epithelial-like cells include, but are not limited to, increased expression of one or more biomarkers associated with the epithelial state, such as E-cadherin, CD24, CD104, MUC-1, MUC-4, MUC16, A33, CD143, CD166, PD-L1, B7-H2, B7-H3, Nectin-1, Nectin-2, Nectin-3, Nectin-4, cytokeratin, ZO-1, Laminin-1, Entactin, collagen, one or more miR200 family microRNA, or mir-335; phenotypic properties of an epithelial cell, such as cellular morphology; sensitivity to chemotherapeutic agents; and any additional functional property as described herein. Epithelial cells or epithelial-like cells are also characterized by decreased expression of one or more proteins associated with the mesenchymal state, such as CD44, CD45, N-cadherin, Fibronectin, Snail, Slug, Twist, Zeb1, CD44, and Vimentin, or a reduction in any phenotype, morphology or functional property associated with mesenchymal cells. Any characteristic of the cell, including expression of a biomarker, may be evaluated.

Examples of characteristics of mesenchymal cells or mesenchymal-like cells include, without limitation, increased expression of one or more mesenchymal proteins, such as CD44, CD45, N-cadherin, Fibronectin, Snail, Slug, Twist, Zeb1, CD44, and Vimentin; phenotypic properties of a mesenchymal cell, such as cellular morphology; resistance to chemotherapeutic agents, and any additional functional property as described herein. Mesenchymal cells or mesenchymal-like cells are also characterized by decreased expression of one or more proteins associated with the epithelial state, such as E-cadherin or CD24, or a reduction in any phenotype, morphology, of functional property associated with epithelial cells.

The tumor cell encompassed by the methods of the disclosure can be, for example, a breast cancer cell, a large intestinal cancer cell, a lung cancer cell, a small cell lung cancer cell, a stomach cancer cell, a liver cancer cell, a blood cancer cell, a bone cancer cell, a pancreatic cancer cell, a skin cancer cell, a head or neck cancer cell, a cutaneous or intraocular melanoma cell, a uterine sarcoma cell, an ovarian cancer cell, a rectal or colorectal cancer cell, an anal cancer cell, a colon cancer cell, a fallopian tube carcinoma cell, an endometrial carcinoma cell, a cervical cancer cell, a vulval cancer cell, a vaginal carcinoma cell, a Hodgkin's disease cell, a non-Hodgkin's lymphoma cell, an esophageal cancer cell, a small intestine cancer cell, an endocrine cancer cell, a thyroid cancer cell, a parathyroid cancer cell, an adrenal cancer cell, a soft tissue tumor cell, an urethral cancer cell, a penile cancer cell, a prostate cancer cell, a chronic or acute leukemia cell, a lymphocytic lymphoma cell, a bladder cancer cell, a kidney cancer cell, a ureter cancer cell, a renal cell carcinoma cell, a renal pelvic carcinoma cell, a CNS tumor cell, a primary CNS lymphoma cell, a bone marrow tumor cell, a brain stem nerve gliomas cell, a pituitary adenoma cell, a testicular cancer cell, an oral cancer cell, a pharyngeal cancer cell, or a uveal melanoma cell.

Method for identifying a compound (e.g., screening compounds) that inhibits tumor growth or metastasis are provided. The methods comprise introducing a test compound into any of the horizontal flow bioreactors disclosed herein and assessing the efficacy of the test compound in inhibiting tumor growth or metastasis.

The test compound can be assessed for an ability to, for example, inhibit tumor cells from undergoing an epithelial to mesenchymal transition at the primary site scaffold, inhibit the migration of tumor cells from the primary site scaffold to the secondary site scaffold, inhibit the attachment of circulating tumor cells to the secondary site scaffold, or inhibit tumor cells from undergoing an epithelial to mesenchymal transition at the secondary site scaffold.

Properties of cells may be assessed by methods known in the art. Cellular morphology can be evaluated by microscopy methods including, for example, bright field, confocal, electron, and fluorescence microscopy. The expression level of cell markers associated with the epithelial state or the mesenchymal state can be measured by methods including quantitative RT-PCR, flow cytometry, cell staining, antibody detection of cell markers, Western blotting, fluorescence microscopy, and mass spectrometry. The migratory ability of cells can be assessed, for example, by a wound closure assay. The invasion and metastatic abilities of a cell can be evaluated, for example, by Matrigel invasion. Cells can be further evaluated for sensitivity to chemotherapeutic agents. Following exposure of the cell to a chemotherapeutic agent, its viability can be assessed by methods known in the art, including proliferation, metabolic activity, and live/dead staining. In certain embodiments, the expression of at least one biomarker associated with the mesenchymal state or the epithelial state is analyzed.

Compounds, or compositions comprising such compounds, that inhibit tumor cells from undergoing an epithelial to mesenchymal transition inhibit the migration of tumor cells, inhibit the attachment of circulating tumor cells, or inhibit tumor cells from undergoing an epithelial to mesenchymal transition, identified by the methods described herein, can be used in methods for treating tumors or tumor metastases in a patient.

From the foregoing, it can be seen that the present invention accomplishes at least all of the stated objectives.

Glossary

Unless defined otherwise, all technical and scientific terms used above have the same meaning as commonly understood by one of ordinary skill in the art to which embodiments of the present invention pertain.

The terms "a," "an," and "the" include both singular and plural referents.

The term "or" is synonymous with "and/or" and means any one member or combination of members of a particular list.

The terms "invention" or "present invention" are not intended to refer to any single embodiment of the particular invention but encompass all possible embodiments as described in the specification and the claims.

The term "about" as used herein refer to slight variations in numerical quantities with respect to any quantifiable variable. Inadvertent error can occur, for example, through use of typical measuring techniques or equipment or from differences in the manufacture, source, or purity of components.

The term "substantially" refers to a great or significant extent. "Substantially" can thus refer to a plurality, majority, and/or a supermajority of said quantifiable variable, given proper context.

The term "generally" encompasses both "about" and "substantially."

The term "configured" describes structure capable of performing a task or adopting a particular configuration. The term "configured" can be used interchangeably with other similar phrases, such as constructed, arranged, adapted, manufactured, and the like.

Terms characterizing sequential order, a position, and/or an orientation are not limiting and are only referenced according to the views presented.

As used herein, a "biomarker" refers to a molecule (e.g., a protein) that can serve as an indicator of the cell state and/or the cell type.

EXAMPLES

Example 1

In this example, prostate cancer cells were chosen to demonstrate the effect of dynamic conditions enabled with the horizontal flow bioreactor on prostate cancer viability and growth rate as compared to static culture.

Methods

Bone Mimetic Scaffold Preparation

Polycaprolactone/in situ hydroxyapatite nanoclay based (PCL/in situ HAPclay) scaffolds were prepared as per the protocol described in prior studies. In brief, sodium montmorillonite (Na-MMT) clay was modified with an amino acid modifier (5-aminovaleric acid) to increase the d-spacing between the clay sheets. Further, HAP and modified clay were mixed to biomineralize HAP into intercalated nanoclay sheets galleries. Then, PCL and 10% in situ HAP Clay were dissolved in 1, 4-dioxane and subjected the resultant solution to freeze-drying extraction to obtain PCL/in-situ HAP Clay scaffolds. Cylindrical scaffolds with dimensions of 12 mm diameter and 3 mm thickness were utilized during experiments.

Cell Lines and Cell Culture

Human mesenchymal stem cells (hMSCs) (PT-2501) (Lonza) were maintained in a complete growth medium (MSCGM Bulletkit medium (Lonza, PT-3001)). Human prostate cancer cells-PC3 (ATCC® CRL-1435™) were purchased from American Type Culture Collection (ATCC) and maintained in complete growth medium (Kaighn's Modification of Ham's F-12 Medium-ATCC, 30-2004, 10% Fetal Bovine Serum (ATCC, 30-2020), and 1% Pen-Strep antibiotic (Gibco)). The cell cultures were maintained at 37° C. and 5% CO2 in a humidified incubator.

Cell Seeding

The scaffolds were first sterilized under ultraviolet (UV) light for about 1 hour and then immersed the scaffolds into 70% ethanol solution for 12 hours. Further, the scaffolds were washed twice with 1× phosphate buffer saline (PBS). $1\times10^5$ PC3 cells were seeded on each scaffold for viability-related experiments and seeded $5\times10^5$ hMSCs on each scaffold for migration-related experiments. hMSCs were cultured on scaffolds for 23 days for their osteogenic differentiation and mineralized bone formation as described previously, before employing them for migration experiments. The media was refreshed for the bioreactor samples every two days and static samples every other day.

DNA Quantification

DNA quantification assay was performed to assess the proliferation rate of PC3 cells by measuring their DNA content using a kit (ACCUBLUE® Broad Range dsDNA Quantitation Kits). Standard solutions were prepared as per the manufacturer's protocol. For sample preparation, a previously described procedure was followed. Briefly, 10 μl of each standard and diluted sample was mixed with 200 μl of working solution and incubated for 30 min at room temperature in the dark. The fluorescence was measured at Ex350 nm/Em460 nm using a fluorescence microplate reader (BioTek).

Live Dead Assay

A live-dead assay was performed to evaluate the viability of PC3 cells under static and flow conditions. The scaffolds seeded with PC3 cells were introduced with both live (Calcein AM) and dead (Ethidium Homodimer III-EthD-III) stains at different time points (Day-4 and Day-8) using a standard protocol (Biotium, 30002-T). Briefly, the scaffolds were rinsed twice with PBS and were incubated in 2 μM calcein AM and 4 μM EthD-III in PBS for 30 minutes at room temperature. Next, the scaffolds were imaged under Zeiss Axio Observer Z1 LSM 700 confocal microscope using Ex/Em wavelengths described in the manufacturer's protocol.

Cell Apoptosis by Flow Cytometry

The apoptosis analysis was carried out using the Propidium Iodide (PI)-AnnexinV double staining method as per the standard procedure (Biolegend). Briefly, samples were retrieved from different conditions on Day 4 and Day 8 and washed thoroughly with cold PBS. Cancer cells were harvested from each scaffold by treating them with 500 μl of TRYPLE™ Express enzyme. Next, cancer cells were resuspended in Annexin binding buffer to a concentration of $1\times10^6$ cells/ml. Further, 100 μl of cell suspension of each condition was treated with 5 μl of Fluorescein isothiocyanate (FITC) conjugated Annexin V and 10 μl of PI stains and incubated in the dark for 15 minutes at room temperature. The cell suspension of each sample was further diluted with 400 μl of Annexin binding buffer and analyzed using BD Accuri C6 Flow cytometer.

Gene Expression by RT-qPCR

Scaffold samples containing PC3 cells were retrieved from different culture conditions on Day 8 to assess their apoptosis-related gene expressions. RNA was isolated using TRIzol reagent and purified using Direct-zol RNA MiniPrep kit (Zymo Research). For migration-related gene expressions, PC3 cells were treated with TRIzol reagent after 24 hours of the migration experiment for their RNA isolation. Next, RNA was reverse transcribed to cDNA using random primers and M-MLV reverse transcriptase (Promega), and the mRNA expressions were quantified using SYBR green master mix. The qPCR reaction conditions used during each run include holding stage—95° C., 5 minutes followed by cycling stage—40 cycles of 95° C., 30 seconds and 60° C., 1 min. The expressions of various genes related to apoptosis and migration-TGFβ-1, Caspase-9, Bcl-2, p53, αv, β3, MMP-9, and CXCR4 were analyzed and normalized to the mean of R actin. The details of the primers are provided in Table 1. The relative fold change was calculated using the 2^(−ΔΔCt) comparative method.

TABLE 1

| Gene | Forward primer | Reverse primer |
|---|---|---|
| β actin | 5'-GGCATCGTGATG GACTCC-3' (SEQ ID NO: 1) | 5'-GCTGGAAGGTGG ACAGCG-3' (SEQ ID NO: 2) |
| TGFβ-1 | 5'-AAGTTGGCATGG TAGCCCTT-3' (SEQ ID NO: 3) | 5'-CCCTGGACACCA ACTATTGC-3' (SEQ ID NO: 4) |
| Caspase-9 | 5'-GAGGGAAGCCCA AGCTGTTC-3' (SEQ ID NO: 5) | 5'-GCCACCTCAAAG CCATGGT-3' (SEQ ID NO: 6) |
| p53 | 5'-CGGGATCCATGG AGGAGCCGCAG TCAGAT-3' (SEQ ID NO: 7) | 5'-CCGCTCGAGTTT CTGGGAAGGGACAG AAGA-3' (SEQ ID NO: 8) |
| Bcl-2 | 5'-GGCTGGGATGCC TTTGTG-3' (SEQ ID NO: 9) | 5'-CAGCCAGGAGAA ATCAAACAGA-3' (SEQ ID NO: 10) |
| αv | 5'-GAAAAGAATGAC ACGGTTGC-3' (SEQ ID NO: 11) | 5'-AGTGATGAGATG GTCCCGCT-3' (SEQ ID NO: 12) |
| β3 | 5'-ACTGCCTGTGTG ACTCCGACT-3' (SEQ ID NO: 13) | 5'-CGCGTGGTACAG TTGCAGTAG-3' (SEQ ID NO: 14) |
| MMP-9 | 5'-TGGGCTACGTGA CCTATGACAT-3' (SEQ ID NO: 15) | 5'-GCCCAGCCACCT CCACTCCTC-3' (SEQ ID NO: 16) |
| CXCR4 | 5'-GATCAGCATCGA CTCCTTCA-3' (SEQ ID NO: 17) | 5'-GGCTCCAAGGAA AGCATAGA-3' (SEQ ID NO: 18) |

Transwell Migration Assay

For the transwell migration assay, the bioreactor assembly was customized to better fit the transwell insert and accommodation of bone mimetic scaffold underneath the transwell insert. A total of $4\times10^4$ PC3 cancer cells were seeded into each Transwell insert (Corning, Inc., Corning, NY, USA) of 8.0 μm pore size in 100 μl PC3 media containing 2% FBS and allowed to adhere to the surface for 3 hours. Next, the media was replaced with 100 μl serum (FBS) free media, and the inserts were moved into the bioreactor. The cells were allowed to migrate towards the lower chamber containing complete PC3 media (F-12 K with 10% FBS) and towards tissue-engineered bone with complete PC3 media (F-12 K with 10% FBS). After 24 hours of incubation, cells that remained on top of the filter were gently removed using cotton swabs. The percentage of cells migrated through the filter was measured using Alamar Blue reagent assay (Invitrogen) following the manufacturer's protocol. The fluorescence intensity was measured using excitation 570 nm and emission 600 nm. PC3 cells seeded in the wells without inserts were considered positive control, and fluorescence emitted only by Alamar blue reagent was considered negative control or background signal. The percentage migration was calculated by using the formula.

Western Blot Analysis

PC3 cells were harvested from transwell inserts and protein was extracted using RIPA lysis buffer. Next, total protein was estimated using the Bradford assay (Thermofisher). The proteins were separated using 10% (v/v) SDS-PAGE gels and transferred to 0.2 μm PVDF membrane. The membrane was blocked for 1 hour at RT with blocking buffer (5% bovine serum albumin, 0.05% Tween-20-Alfa Aesar). Next, the membrane was incubated with a primary antibody overnight at 4° C. The primary antibodies used for the analysis were p-Smad2 (Cell signaling #3108, 1:1000 dilution), Smad2 (Cell signaling #3102, 1:1000 dilution), p-Akt1 (Cell signaling #9271, 1:1000 dilution), and Akt (Cell signaling #9272, 1:1000 dilution). Further, the membrane was incubated for 1 hour at room temperature with a horseradish peroxidase-conjugated secondary antibody at 1:5000 dilution. The blots were scanned under a Chemiluminescence imaging system (Applied Biosystems).

Results

Figure 16:
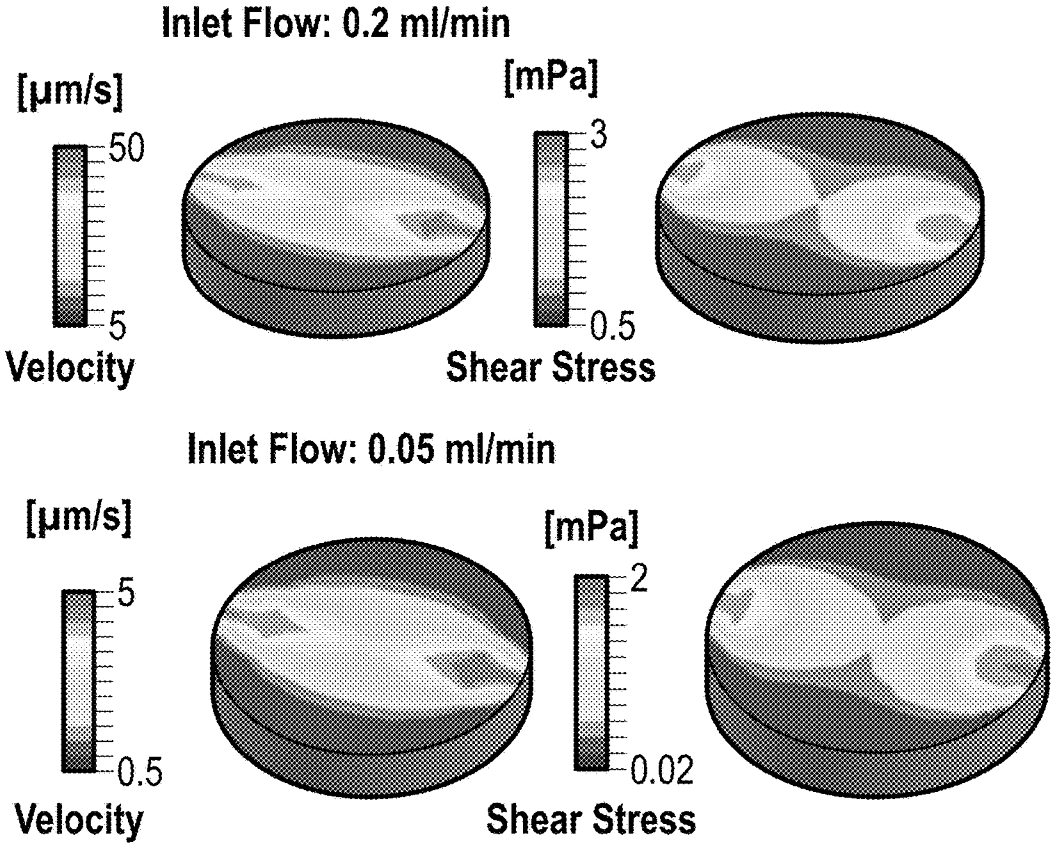
FIG. 16 shows velocity and shear stress distribution on a scaffold surface at inlet flow of 0.2 ml/min and at inlet flow of 0.05 ml/min. Arrows represent the direction of fluid flow.

Optimization of Interstitial Flow Velocities and Shear Stress for Optimum Cell Growth The reported interstitial fluid velocities range in vivo is 0.1-4 μm/s. Here, two different inlet flow rates-0.05 ml/min (low flow rate) and 0.2 ml/min (high flow rate)—were analyzed to attain physiological interstitial fluid velocity range and understand the correlation between fluid shear stress and cellular response. The simulated fluid flow on the scaffold surface analyzed by CFD—displayed heterogeneous fluid velocity and shear stress magnitudes. The velocity range attained at different flow rates were 5.0 μm/s (velmin) and 50 μm/s (velmax), and 0.5 μm/s (velmin) and 5.0 μm/s (velmax) corresponding to 0.2 ml/min and 0.05 mL/min, respectively. The fluid shear stress estimated for 0.2 ml/min ranged between 0.5 mPa and 3 mPa, while 0.05 mL/min ranged between 0.02 and 2 mPa. The color gradient indicates faster flow in the scaffold's center than the stagnant fluid layer near the wall (FIG. 16). From CFD results, it was concluded that the physiological velocity was achieved at a 0.05 ml/min flow rate. However, to understand the effect of high flow rate on cellular response and to optimize flow rate experimentally, a cell viability assay was performed using both flow rates.

High Flow Rate Inhibits Cell Growth and Induces Apoptosis

Figure 15:
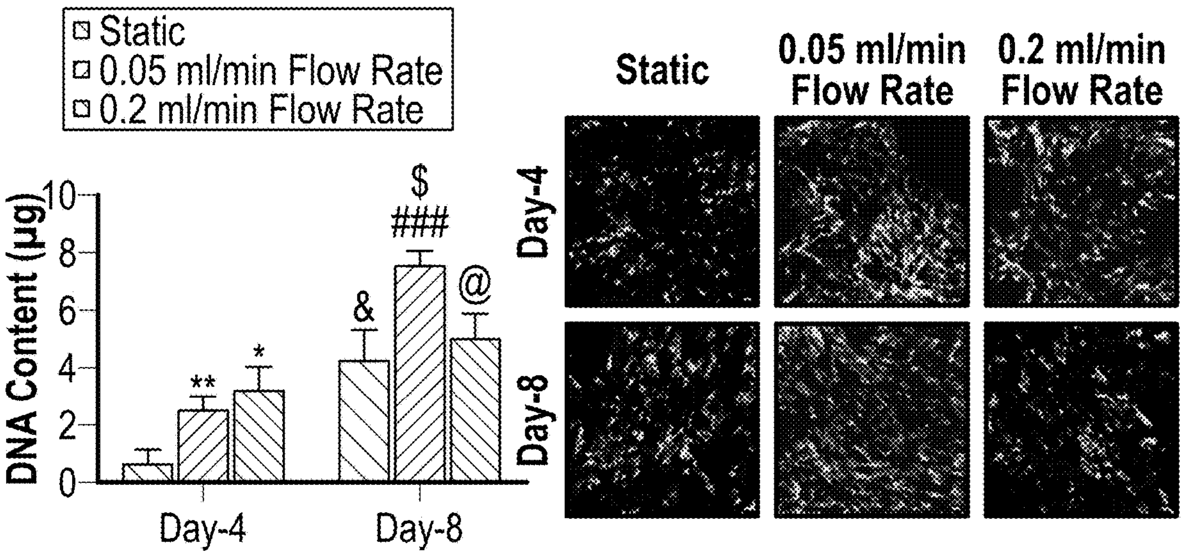
FIG. 15 shows cell viability assessed on Day-4 and Day-8 using a static culture (control), 0.05 ml/min flow rate, and 0.2 ml/min flow rate by charting DNA content (left) and capturing images of a live-dead assay (right). Scale bar 100 μm. $^*p<0.05$ and $^{**}p<0.01$ indicates a significant difference between the static sample and different flow rates samples at Day-4. $^{\&}p<0.05$ indicates a significant difference between the static sample at Day-4 and Day-8. $^{\#\#\#}p<0.001$ indicates a significant difference between 0.05 ml/min flow rate sample at Day-4 and Day-8. $^{\$}p<0.05$ indicates a significant difference between the static sample at Day-8 and 0.05 ml/min flow rate sample at Day-8. $^{@}p<0.05$ indicates a significant difference between the 0.05 ml/min flow rate sample at Day-8 and 0.2 ml/min flow rate sample at Day-8.

To assess the viability of PC3 cells under static and different flow conditions, their DNA content was measured. The DNA content of PC3 cells at Day-4 was significantly higher under both 0.2 ml/min (*$p<0.05$) and 0.05 ml/min ($p<0.01$) flow conditions compared to static culture. Similarly, at Day-8, significantly higher DNA content of PC3 under 0.05 ml/min ($^{\$}<p<0.05$) compared to their static culture was observed. However, the DNA content of PC3 cells under 0.2 ml/min flow rate was significantly decreased ($^{@}p<0.05$) compared to 0.05 ml/min flow rate conditions (FIG. 15**). Live-dead staining assay revealed similar outcomes, representing a reduced population of live cells under high flow rate conditions at Day-8 compared to low flow rate conditions.

To investigate the possible reason for decreased cell growth of PC3 cells under high flow rate, a cell apoptosis assay by flow cytometry was performed. Significant changes in the apoptosis rate at Day-4 between 0.2 ml/min and 0.05 ml/min flow rates were not observed; however, at Day-8, a significantly higher percentage of apoptotic cells (22.60±0.55%) cultured under a high flow rate compared to low flow rate conditions (11.01±0.50%) was observed, indicating 0.2 ml/min flow rate is not suitable for PC3 cells growth for a prolonged period (FIG. 14).

Next, to investigate the molecular mechanism responsible for apoptotic induction of PC3 cells at Day-8 under a high flow rate, apoptosis-related genes were examined. mRNA levels of tumor suppressor gene, p53 (*$p<0.01$) and apoptotic gene, caspase-9 ($p<0.01$) were significantly upregulated in PC3 cells under high flow rate while expressions of antiapoptotic gene, Bcl-2 (*$p<0.01$) were downregulated, suggesting apoptotic induction in PC3 cells under high flow rate. mRNA levels of TGF-β1 were also examined, which is highly accountable for apoptotic induction in tumor cells. S significant upregulation in TGF-β1 mRNA levels (*$p<0.001$) were observed under high flow rate compared to low flow rate conditions. It is also reported that TGF-β1 acts as both a tumor suppressor and tumor inducer, promoting cell apoptosis via Smad-dependent pathway while suppressing apoptosis or enhancing cell survival via Smad independent-PI3K/Akt pathway. Thus, the feasibility of these two signaling pathways was investigated to understand the possibility of an increase in TFG-β1 mRNA levels at high flow rate conditions. Significantly high protein expression of p-Smad2 under high flow rate conditions compared to low flow rate conditions, indicating tumor suppressor effect of TGF-β1 under high flow conditions. In addition, a thick band of p-Akt under low flow conditions was observed while a very thin p-Akt band under high flow rate conditions, suggesting that the survival of PC3 cells was decreased under high flow conditions (FIG. 14).

Figure 17:
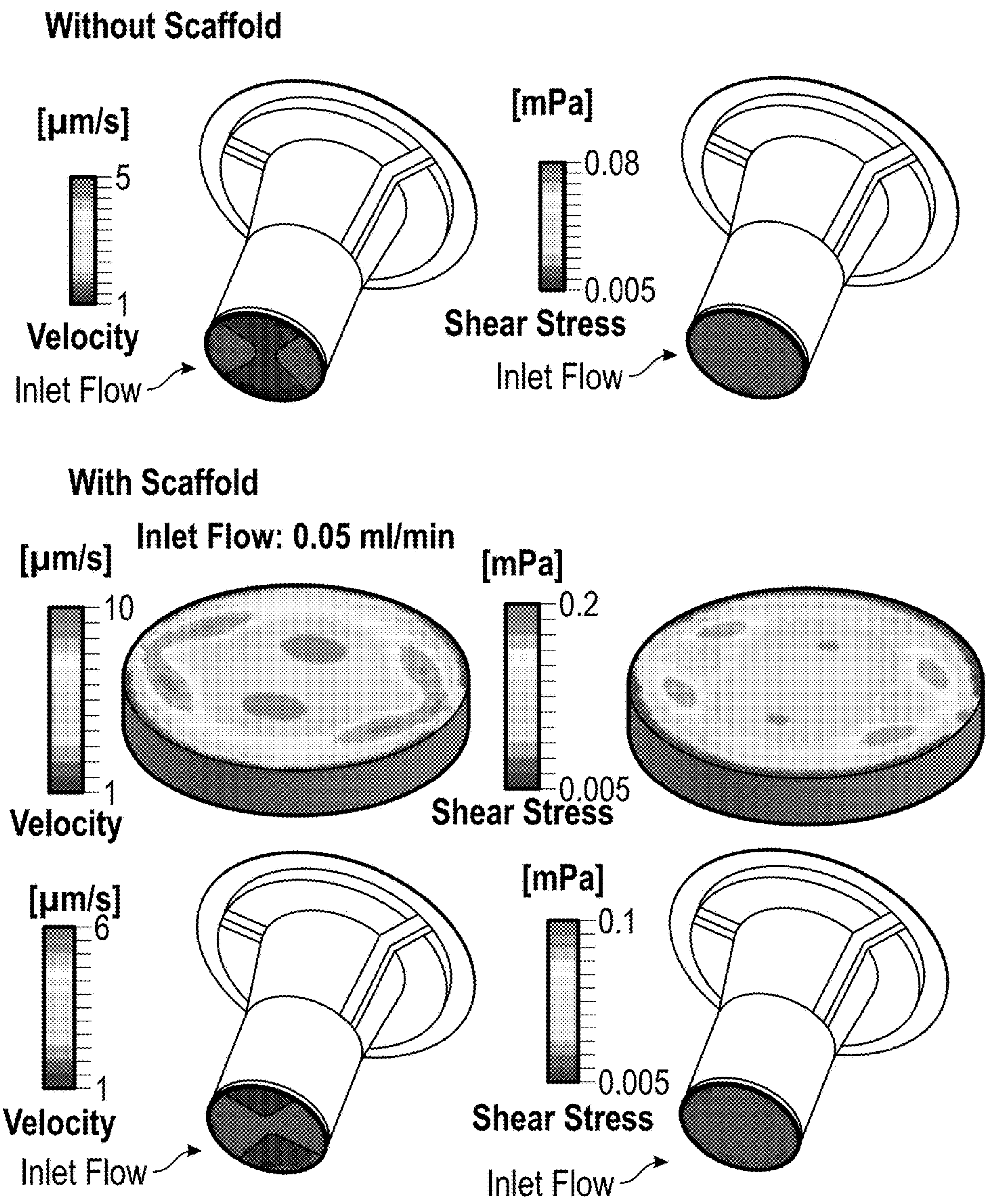
FIG. 17 shows velocity and shear stress distribution on transwell membrane surface at inlet flow of 0.05 ml/min for a bioreactor assembly with a transwell insert and without a scaffold (top) and for a bioreactory with a transwell insert and a scaffold (bottom). Arrows represent the direction of fluid flow.
Figure 18A:
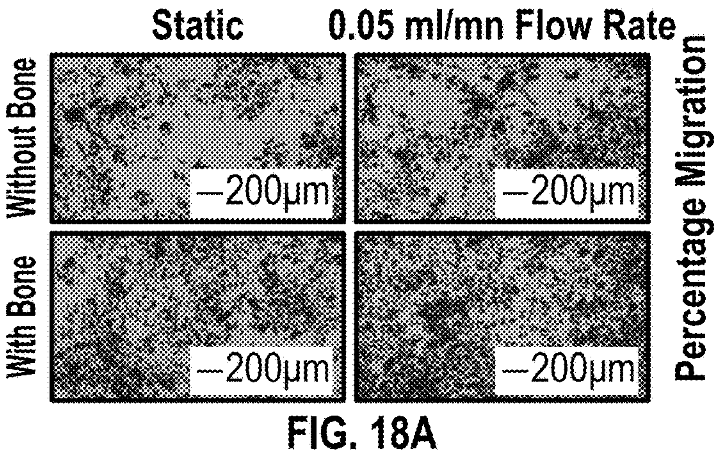
FIGS. 18A-18D show transmembrane invasion assays. 18A: migration of PC3 cancer cells through transwell inserts with and without bone under static and dynamic culture. Migrated cells are stained with crystal violet dye. 18B: Percentage cell migration was determined using Alamar Blue assay. 18C: Gene expression of migration-related genes was determined by RT-qPCR. 18D: Also shown is a proposed mechanism of CXCR4 and αvβ3 integrins mediated increase in MMP-9 levels under dynamic conditions in the presence of bone. $^*p<0.05$, $^{}p<0.01$, and $^{*}p<0.001$ indicates a significant difference between the static sample without bone and other conditions. $\#p<0.05$ and $\#\#p<0.01$ indicates a significant difference between the dynamic sample without bone and other conditions. $\&p<0.05$ indicates a significant difference between the static sample with bone and dynamic sample with bone.
Figure 18B:
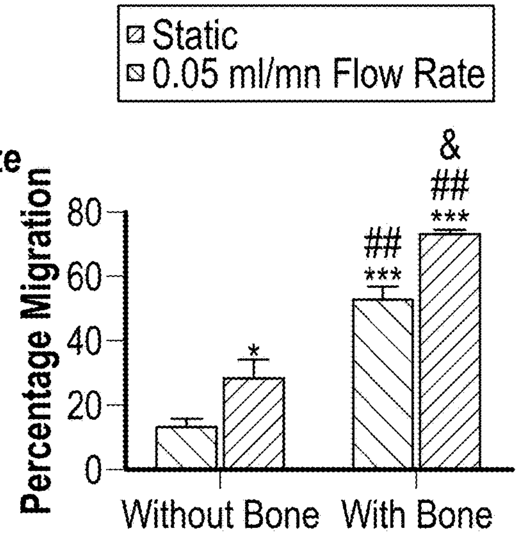
Figure 18C:
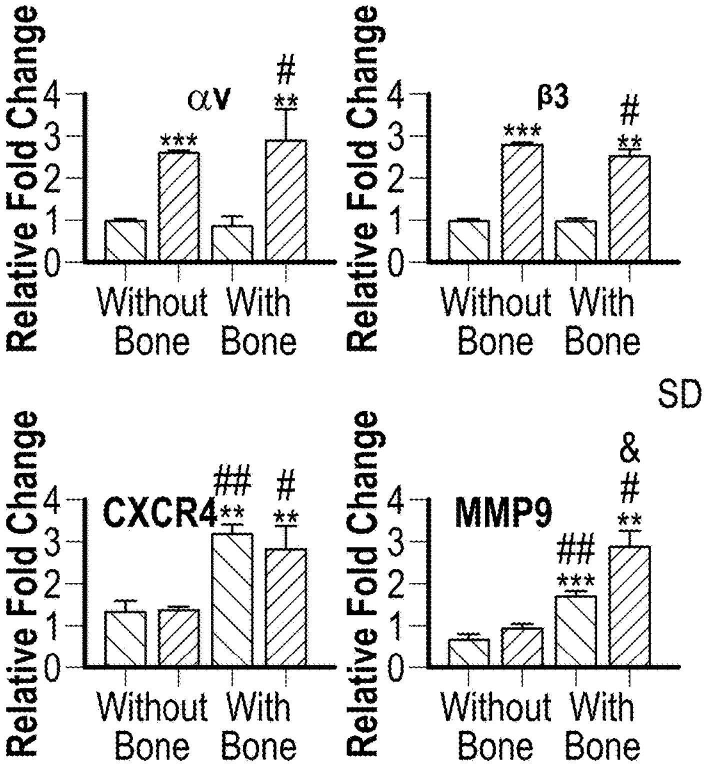
Figure 18D:
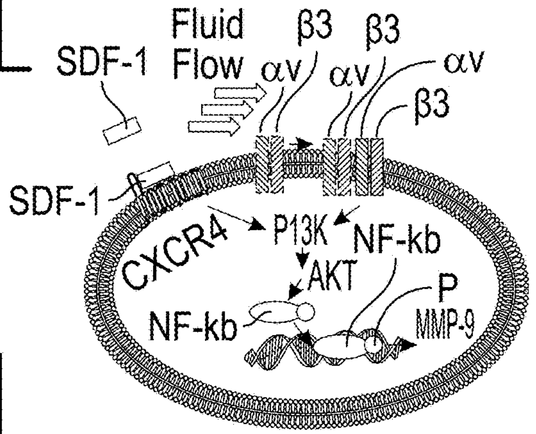
Figure 19:
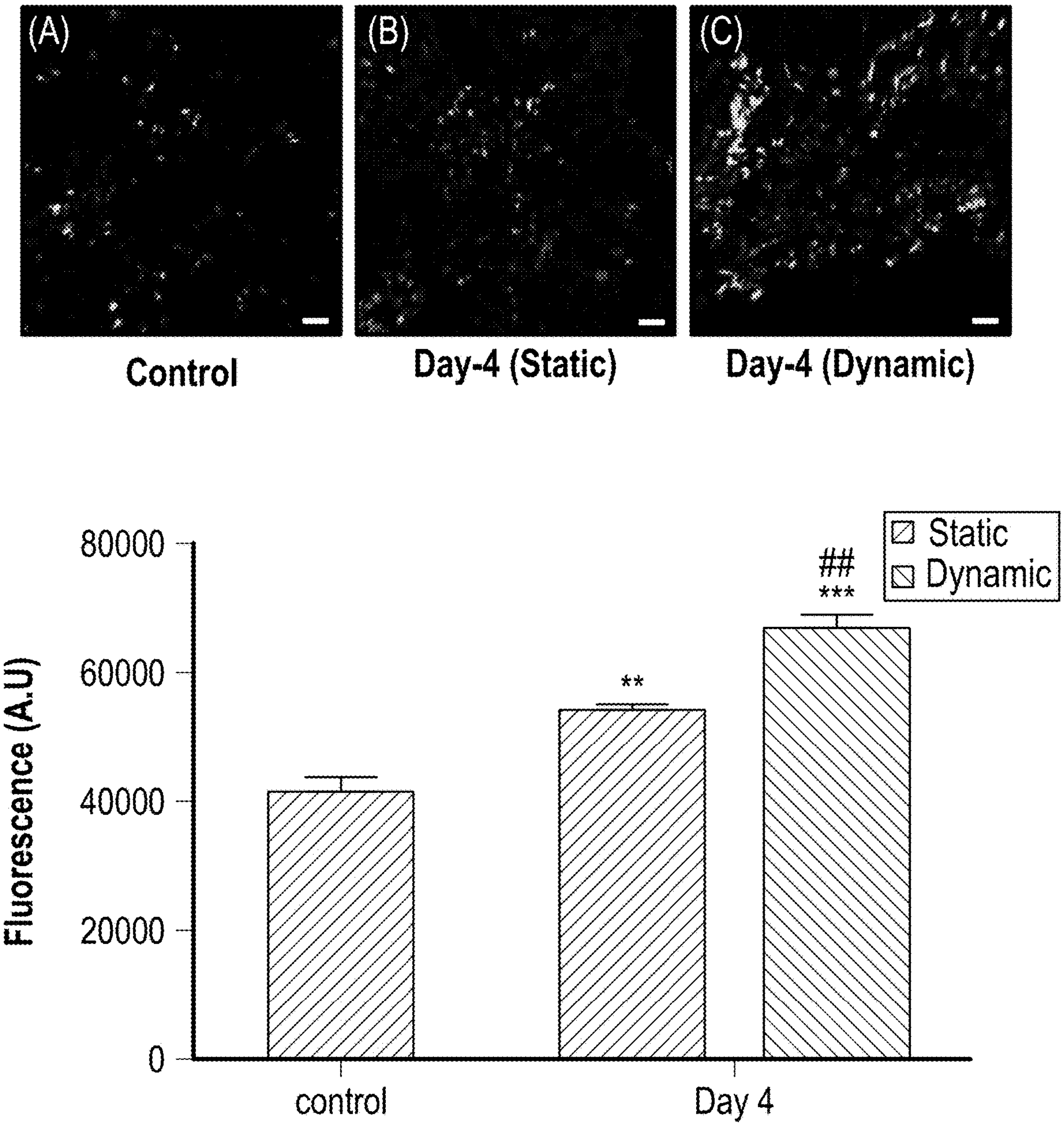
FIG. 19 shows the proliferation and osteogenic differentiation of hMSCs grown on scaffolds under static vs. dynamic culture.
Figure 20:
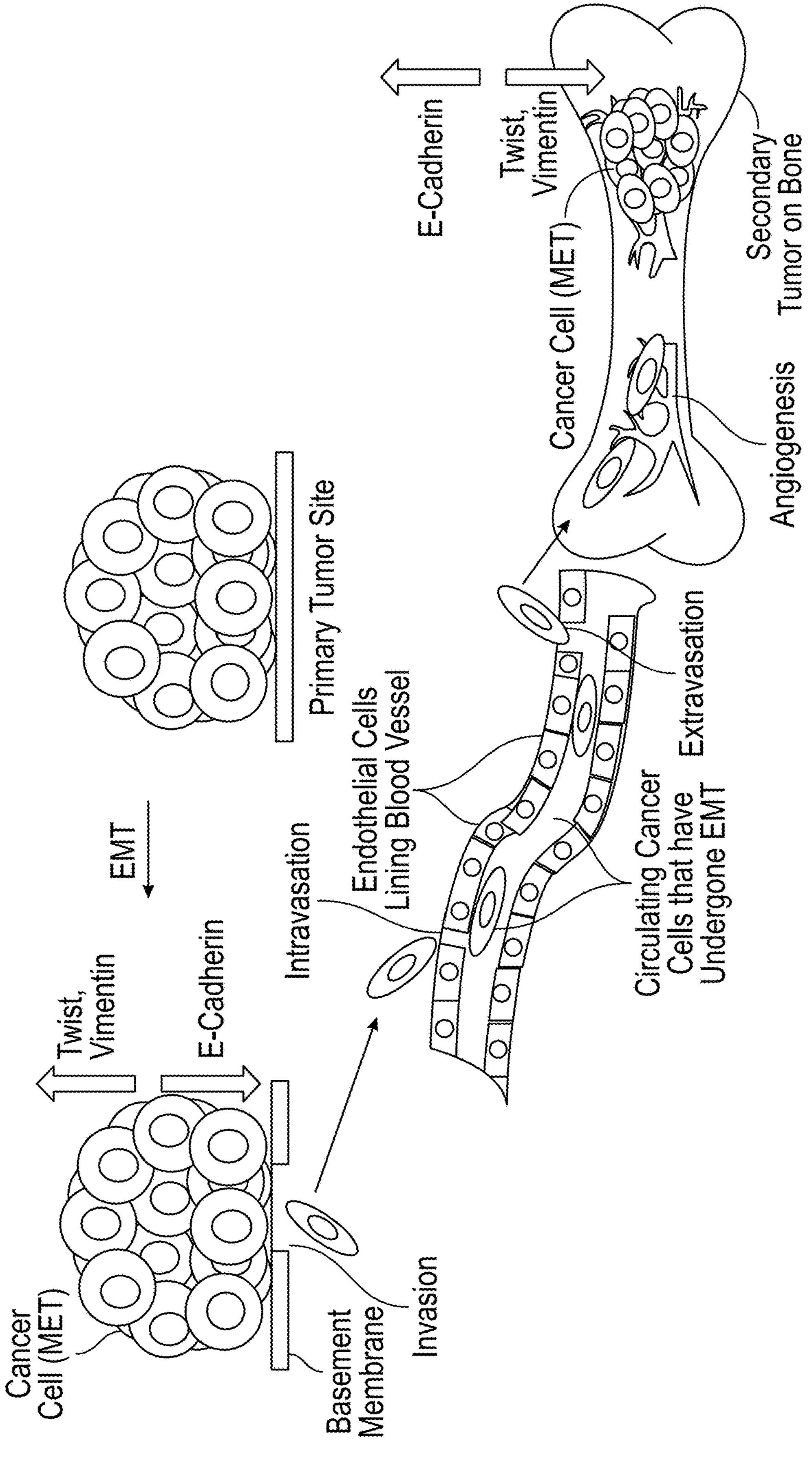
FIG. 20 shows mesenchymal to epithelial transition (MET) of advanced staged prostate cancer.
Figure 21:
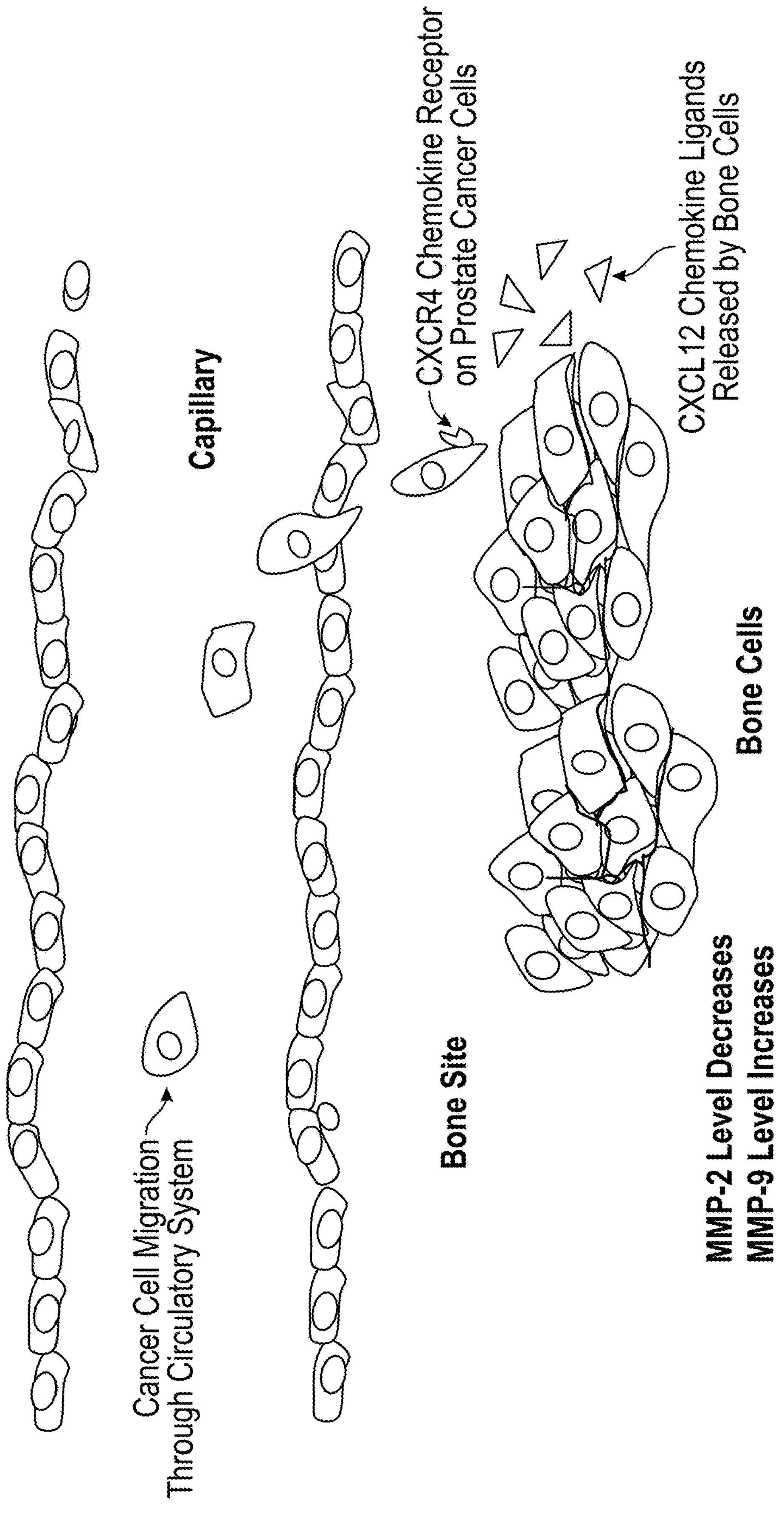
FIG. 21 shows extravasation of prostate cancer cells.
Figure 22:
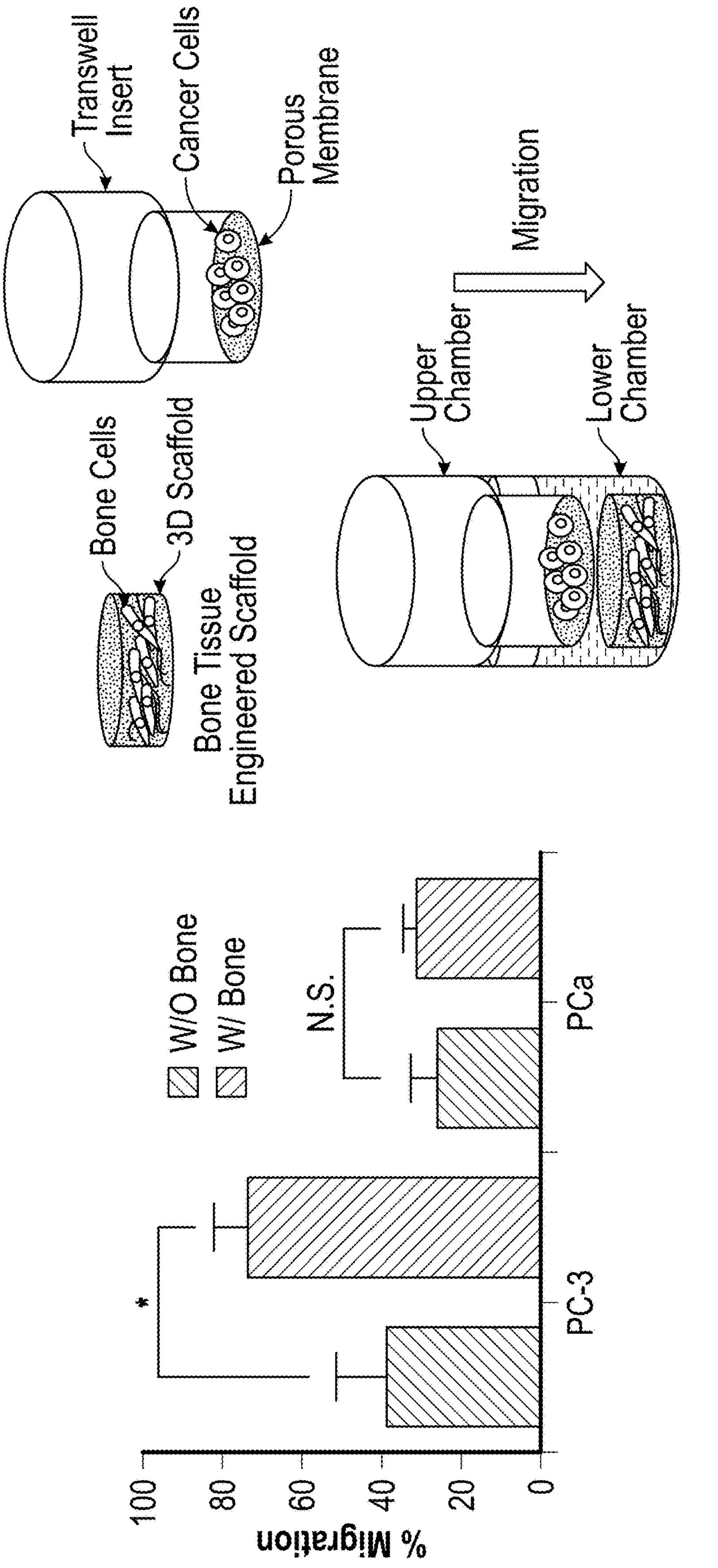
FIG. 22 shows enhanced migration of PC3 cells under dynamic culture.
Figure 23:
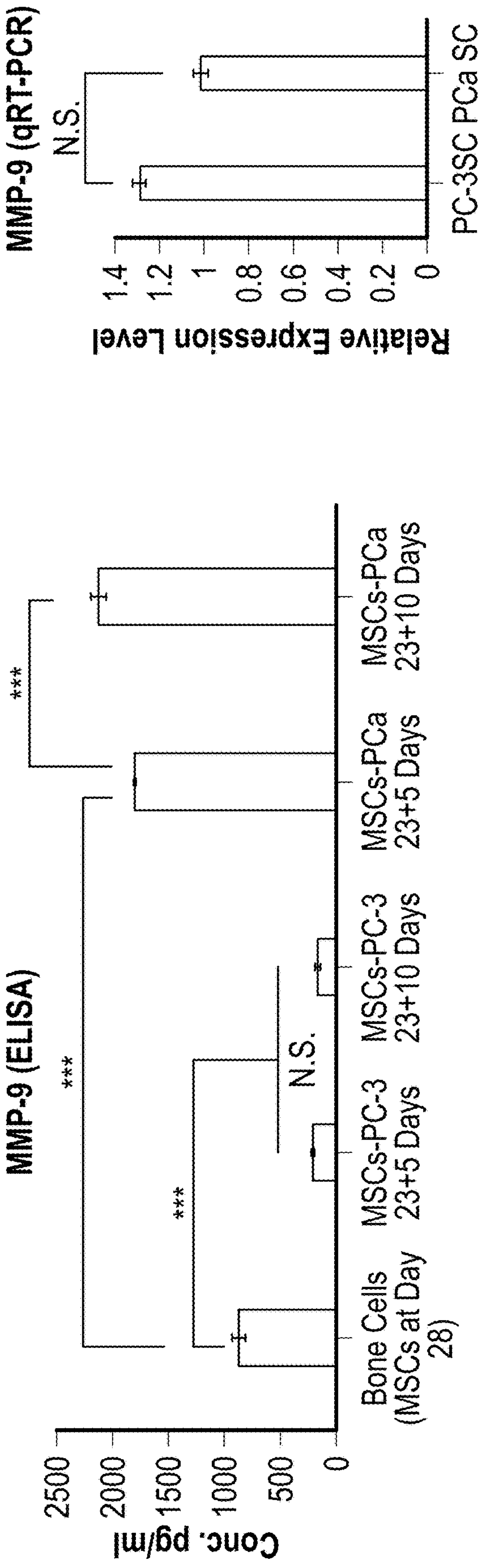
FIG. 23 shows MMP 9 levels were affected during prostate cancer progression on bone.

Physiological Interstitial Fluid Velocity Induces a High Migration Rate of Prostate Cancer Cells To evaluate the migration of PC3 cells through transwell insert under flow conditions, a 0.05 ml/min flow rate was employed based on the CFD and viability (FIG. 17) results. From CFD analysis using transwell insert without scaffold, it was demonstrated that shear stress attained at the membrane of transwell insert ranged between 0.005 mPa and 0.08 mPa, which was nearly equivalent to shear stress range (0.005 mPa-0.1 mPa) at the membrane of transwell insert in the presence of scaffold, indicating that similar fluid derived shear stress acting on PC3 cells in the presence or absence of tissue-engineered bone.

First, the migration rate of PC3 cells under static and dynamic conditions without placing a bone-containing scaffold underneath the transwell insert to understand the effect of continuous fluid flow on migration rate. After 24 hours of incubation, the percentage migration of PC3 cells under fluid flow was increased by ~2-fold (28.64±5.61%) compared to cells under static condition (13.51±2.47%), indicating the effect of fluid flow on the migration rate of PC3 cells. Next, the effect of flow conditions on cell migration rate in the presence of bone was evaluated. The overall percentage migration through the transwell insert was increased in the presence of tissue-engineered bone under both culturing conditions; however, under dynamic conditions, the percentage of cell migration (73.24±1.05%) was significantly higher ($^{\&}p<0.01$) than static culture (52.95±4.08%) (FIG. 18). Thus, to investigate the molecular mechanism responsible for the observed change in percentage cell migration under flow conditions and in the presence of bone, migration-related gene expression under different culture conditions was examined.

αvβ3 Integrins Activation Via Fluid Flow Promotes Percentage Cell Migration

Fluid shear stress activates αvβ3 integrins that convert mechanical stimulation into chemical signals inside the cells and activate downstream signals. The mRNA levels of αv (*$p<0.001$) and 33 (*$p<0.001$) integrins in PC3 cells were significantly upregulated under dynamic conditions compared to static conditions. Next, MMP-9 gene expression was investigated and mRNA levels of MMP-9 were also significantly upregulated under dynamic conditions (*$p<0.05$) compared to static conditions in the absence of bone, indicating the effect of fluid shear stress on cancer cells migration. mRNA levels of αv, β3, and MMP-9 in PC3 cells in the presence of tissue-engineered bone under both dynamic and static culture conditions. The results showed that mRNA levels of αv and β3 in PC3 cells in the presence of bone were not significantly different from without bone samples. However, expression levels of MMP-9 in PC3 cells in the presence of bone were significantly higher than in the absence of bone under dynamic conditions, indicating the role of other factors in the overall increase in cell migration (FIG. 18).

CXCR4 CXCL12 Interaction Leads to Increased Percent Cell Migration in the Presence of Bone CXCR4 is a crucial regulator of prostate cancer invasiveness and metastasis development. High CXCR4 expression in prostate cancer cells is associated with their propensity to metastasize to the bone, a tissue that expresses a high level of the chemokine CXCL12. As our results showed upregulation in MMP-9 levels in the presence of bone, it was hypothesized that CXCR4 activation led to an increase in MMP-9 levels. Thus, CXCR4 mRNA levels of PC3 cells in the presence and absence of bone under both conditions were investigated. A significant increase in CXCR4 levels in the presence of bone under both conditions compared to the without bone scaffolds was observed. CXCR4 mRNA levels were not significantly changed in the presence of bone under static and dynamic conditions, indicating that CXCR4 activation in PC3 cells is not influenced by flow conditions but by the bone. However, significant upregulation in MMP-9 levels in the presence of bone under dynamic conditions suggesting a synergistic effect of CXCR4 and αvβ3 integrins in increased migration rate.

The "scope" of the present invention is defined by the appended claims, along with the full scope of equivalents to which such claims are entitled. The scope of the invention is further qualified as including any possible modification to any of the aspects and/or embodiments disclosed herein which would result in other embodiments, combinations, subcombinations, or the like that would be obvious to those skilled in the art.

What is claimed is:

1. A horizontal flow bioreactor comprising:
 a primary site having cells, said primary site fluidly terminating at a media inlet or a surface of a transwell insert;
 a scaffold placed between the media inlet and a media outlet;
 a secondary site fluidly beginning at said media outlet;
 a horizontal fluid path over and through said scaffolds for migrating said cells from the primary site to the secondary site;
 wherein the primary site is an upper bioreactor chamber and the secondary site is a lower bioreactor chamber; and
 wherein flow mimics interstitial fluid flow conditions around the cells.

2. The horizontal flow bioreactor of claim 1 further comprising a drain.

3. The horizontal flow bioreactor of claim 1, wherein the cells are tumor cells.

4. An incubator comprising:
 a plurality the horizontal flow bioreactors of claim 1;
 an epithelial to mesenchymal transition (EMT) test-bed comprising some of the horizontal flow bioreactors;
 a multi-channel pump; and
 a mesenchymal to epithelial transition (MET) test-bed comprising some of the horizontal flow bioreactors.

5. The incubator of claim 4 wherein a number of horizontal flow bioreactors in the EMT test-bed and a number of horizontal flow bioreactors in the MET test-bed are identical, wherein the horizontal flow bioreactors within the EMT test-bed are fluidly arranged in parallel and the horizontal flow bioreactors within the MET test-bed are fluidly arranged in parallel.

6. A method for modeling tumor growth and metastasis in vitro, the method comprising:
 providing a horizontal flow bioreactor comprising a first bioreactor chamber; a second bioreactor chamber; a peristaltic pump that can regulate flow rate of a fluid; tubing for delivering the fluid between the pump, the first bioreactor chamber, the second bioreactor chamber; and an in-line injection port for sample insertion and/or sample extraction;
 introducing tumor cells into the horizontal flow bioreactor;
 flowing a medium from the first bioreactor chamber to the second bioreactor chamber, wherein the flow mimics interstitial fluid flow conditions around the cells.

7. The method of claim 6, wherein the first bioreactor chamber comprises a primary site scaffold, and wherein the second bioreactor chamber comprises a secondary site scaffold.

8. The method of claim 7, wherein the secondary site scaffold is a bone mimetic scaffold, a lung mimetic scaffold, a liver mimetic scaffold, or a brain mimetic scaffold.

9. The method of claim 6, wherein the introducing comprises seeding the tumor cells on a primary site scaffold in the first bioreactor chamber.

* * * * *

SEQUENCE LISTING

```
Sequence total quantity: 18
SEQ ID NO: 1              moltype = DNA  length = 18
FEATURE                   Location/Qualifiers
source                    1..18
                          mol_type = other DNA
                          organism = synthetic construct
SEQUENCE: 1
ggcatcgtga tggactcc                                                18

SEQ ID NO: 2              moltype = DNA  length = 18
FEATURE                   Location/Qualifiers
source                    1..18
                          mol_type = other DNA
                          organism = synthetic construct
SEQUENCE: 2
gctggaaggt ggacagcg                                                18

SEQ ID NO: 3              moltype = DNA  length = 20
FEATURE                   Location/Qualifiers
source                    1..20
                          mol_type = other DNA
                          organism = synthetic construct
SEQUENCE: 3
aagttggcat ggtagccctt                                              20

SEQ ID NO: 4              moltype = DNA  length = 20
FEATURE                   Location/Qualifiers
source                    1..20
                          mol_type = other DNA
                          organism = synthetic construct
SEQUENCE: 4
ccctggacac caactattgc                                              20

SEQ ID NO: 5              moltype = DNA  length = 20
FEATURE                   Location/Qualifiers
source                    1..20
                          mol_type = other DNA
                          organism = synthetic construct
SEQUENCE: 5
gagggaagcc caagctgttc                                              20

SEQ ID NO: 6              moltype = DNA  length = 19
FEATURE                   Location/Qualifiers
source                    1..19
                          mol_type = other DNA
                          organism = synthetic construct
SEQUENCE: 6
gccacctcaa agccatggt                                               19

SEQ ID NO: 7              moltype = DNA  length = 29
```

-continued

```
FEATURE                Location/Qualifiers
source                 1..29
                       mol_type = other DNA
                       organism = synthetic construct
SEQUENCE: 7
cgggatccat ggaggagccg cagtcagat                                 29

SEQ ID NO: 8           moltype = DNA  length = 30
FEATURE                Location/Qualifiers
source                 1..30
                       mol_type = other DNA
                       organism = synthetic construct
SEQUENCE: 8
ccgctcgagt ttctgggaag ggacagaaga                                30

SEQ ID NO: 9           moltype = DNA  length = 18
FEATURE                Location/Qualifiers
source                 1..18
                       mol_type = other DNA
                       organism = synthetic construct
SEQUENCE: 9
ggctgggatg cctttgtg                                             18

SEQ ID NO: 10          moltype = DNA  length = 22
FEATURE                Location/Qualifiers
source                 1..22
                       mol_type = other DNA
                       organism = synthetic construct
SEQUENCE: 10
cagccaggag aaatcaaaca ga                                        22

SEQ ID NO: 11          moltype = DNA  length = 20
FEATURE                Location/Qualifiers
source                 1..20
                       mol_type = other DNA
                       organism = synthetic construct
SEQUENCE: 11
gaaaagaatg acacggttgc                                           20

SEQ ID NO: 12          moltype = DNA  length = 20
FEATURE                Location/Qualifiers
source                 1..20
                       mol_type = other DNA
                       organism = synthetic construct
SEQUENCE: 12
agtgatgaga tggtcccgct                                           20

SEQ ID NO: 13          moltype = DNA  length = 21
FEATURE                Location/Qualifiers
source                 1..21
                       mol_type = other DNA
                       organism = synthetic construct
SEQUENCE: 13
actgcctgtg tgactccgac t                                         21

SEQ ID NO: 14          moltype = DNA  length = 21
FEATURE                Location/Qualifiers
source                 1..21
                       mol_type = other DNA
                       organism = synthetic construct
SEQUENCE: 14
cgcgtggtac agttgcagta g                                         21

SEQ ID NO: 15          moltype = DNA  length = 22
FEATURE                Location/Qualifiers
source                 1..22
                       mol_type = other DNA
                       organism = synthetic construct
SEQUENCE: 15
tgggctacgt gacctatgac at                                        22

SEQ ID NO: 16          moltype = DNA  length = 21
FEATURE                Location/Qualifiers
source                 1..21
                       mol_type = other DNA
                       organism = synthetic construct
SEQUENCE: 16
gcccagccac ctccactcct c                                         21
```

-continued

```
SEQ ID NO: 17          moltype = DNA  length = 20
FEATURE                Location/Qualifiers
source                 1..20
                       mol_type = other DNA
                       organism = synthetic construct
SEQUENCE: 17
gatcagcatc gactccttca                                          20

SEQ ID NO: 18          moltype = DNA  length = 20
FEATURE                Location/Qualifiers
source                 1..20
                       mol_type = other DNA
                       organism = synthetic construct
SEQUENCE: 18
ggctccaagg aaagcataga                                          20
```